United States Patent
Beckman et al.

(10) Patent No.: US 11,766,302 B2
(45) Date of Patent: Sep. 26, 2023

(54) ROBOTIC SURGICAL TOOL WITH PIVOTABLE TRANSMISSION LINKAGE ON TRANSLATING CARRIAGE

(71) Applicant: Cilag GmbH International, Zug (CH)

(72) Inventors: Andrew T. Beckman, Cincinnati, OH (US); Charles J. Scheib, Loveland, OH (US); Travis Schuh, Los Altos, CA (US); Ben Dickerson, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 371 days.

(21) Appl. No.: 16/946,432

(22) Filed: Jun. 22, 2020

(65) Prior Publication Data

US 2021/0393348 A1 Dec. 23, 2021

(51) Int. Cl.

| | |
|---|---|
| *A61B 34/37* | (2016.01) |
| *B25J 9/10* | (2006.01) |
| *A61B 34/00* | (2016.01) |
| *B25J 5/02* | (2006.01) |
| *B25J 5/00* | (2006.01) |
| *B25J 15/02* | (2006.01) |
| *B25J 19/00* | (2006.01) |

(52) U.S. Cl.
CPC .............. *A61B 34/37* (2016.02); *A61B 34/74* (2016.02); *B25J 5/007* (2013.01); *B25J 5/02* (2013.01); *B25J 9/1035* (2013.01); *B25J 15/026* (2013.01); *B25J 19/005* (2013.01)

(58) Field of Classification Search
None
See application file for complete search history.

(56) References Cited

U.S. PATENT DOCUMENTS

| | | |
|---|---|---|
| 10,189,157 B2 | 1/2019 | Schlegel et al. |
| 2008/0167663 A1 | 7/2008 | De Mathelin et al. |
| 2012/0215220 A1* | 8/2012 | Manzo ............... A61B 18/1482 606/46 |
| 2014/0005718 A1* | 1/2014 | Shelton, IV ........... A61B 34/30 606/205 |

(Continued)

FOREIGN PATENT DOCUMENTS

EP 0512867 A2 11/1992

OTHER PUBLICATIONS

ISR-WO for related matter PCT/EP2021/066795 dated Dec. 21, 2021.

*Primary Examiner* — Tamara L Weber
(74) *Attorney, Agent, or Firm* — Vorys, Sater, Seymour and Pease LLP

(57) ABSTRACT

A robotic surgical tool includes a drive housing having first and second ends, a carriage movably mounted to the drive housing, and a shaft extending from the carriage and penetrating the first end, the shaft having an end effector arranged at a distal end. An activating mechanism is secured to the carriage and includes a transmission link pivotably coupled to the carriage, a transmission drive gear rotatably mounted to a transmission link, a drive gear rotatably mounted to the carriage and operatively coupled to the transmission drive gear, and a transmission driven gear rotatably mounted to the transmission link and driven by rotation of the transmission drive gear. The transmission link is pivotable between a first and second positions to actuate the activating mechanism to perform first and second functions, respectively, of the end effector.

20 Claims, 21 Drawing Sheets

(56) References Cited

U.S. PATENT DOCUMENTS

| | | | |
|---|---|---|---|
| 2017/0072561 A1* | 3/2017 | Schlegel | B25J 9/1035 |
| 2019/0099227 A1* | 4/2019 | Rockrohr | A61B 34/30 |
| 2020/0275928 A1* | 9/2020 | Shelton, IV | A61B 34/71 |
| 2021/0015572 A1 | 1/2021 | Gomez et al. | |
| 2021/0022815 A1 | 1/2021 | Abbott | |

* cited by examiner

ROBOTIC SURGICAL TOOL WITH PIVOTABLE TRANSMISSION LINKAGE ON TRANSLATING CARRIAGE

TECHNICAL FIELD

The systems and methods disclosed herein are directed to robotic surgical tools and, more particularly to, robotic surgical tools including a carriage movably mounted to a lead screw and a motor coupled to the carriage and operable to operate one or more functions of the robotic surgical tool.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF), and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving the drive cables and/or other mechanical mechanisms manipulates the end effector to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments of the disclosure include a robotic surgical tool that includes a drive housing having a first end, a second end, and a carriage movably mounted to the drive housing, an elongate shaft extending from the carriage and penetrating the first end, the shaft having an end effector arranged at a distal end thereof, and an activating mechanism secured to the carriage. The activating mechanism includes a transmission link pivotably coupled to the carriage, a transmission drive gear rotatably mounted to a transmission link, a drive gear rotatably mounted to the carriage and operatively coupled to the transmission drive gear such that rotation of the drive gear correspondingly rotates the transmission drive gear, and a transmission driven gear rotatably mounted to the transmission link and driven by rotation of the transmission drive gear, wherein the transmission link is pivotable between a first position, where the transmission driven gear is arranged to actuate the activating mechanism to perform a first function of the end effector, and a second position, where the transmission driven gear is arranged to actuate the activating mechanism to perform a second function of the end effector different from the first function. In a further embodiment, the robotic surgical tool further includes a motor mounted to the carriage and operable to drive the drive gear. In another further embodiment, the activating mechanism further includes a power source communicably coupled to the motor to provide electrical power to the motor, a receiver that receives signals for operation of the motor, and an internal processor communicably coupled to the motor, the power source, and the receiver to regulate operation of the motor based on the signals received from the receiver. In another further embodiment, the power source is an internal power source mounted to the carriage for travel with the carriage. In another further embodiment, the power source is an external power source disposed outside of the drive housing. In another further embodiment, the activating mechanism further comprises a spline extending between the first and second ends, a pinion gear movably coupled to the spline and rotatable with rotation of the spline, and a rack gear pivotably coupled to the transmission link and positioned to engage the pinion gear, wherein rotation of the spline correspondingly rotates the pinion gear to drives the rack gear and thereby pivot the transmission link between the first and second positions. In another further embodiment, the robotic surgical further includes a drive input arranged at the first end and operatively coupled to the spline such that rotation of the drive input correspondingly rotates the spline and the pinion drive gear, and an instrument driver arranged at an end of a robotic arm and matable with the drive housing at the first end, the instrument driver providing a drive output matable with the drive input such that rotation of the drive output correspondingly rotates the drive input and thereby transitions the transmission link between the first and second positions. In another further embodiment, the robotic surgical tool further includes a firing rod extending within the shaft and defining external threads, and a knife located at the end effector and operatively coupled to the firing rod such that movement of the firing rod correspondingly moves the knife in the same direction, wherein, when the transmission link is in the first position, rotation of the transmission driven gear drives the external threads of the firing rod and thereby moves the firing rod and the knife longitudinally. In another further embodiment, the shaft comprises a closure tube that defines external threads, and wherein, when the transmission link is in the second position, rotation of the transmission driven gear drives the external threads and thereby moves the closure tube axially along a longitudinal axis of the shaft to close or open jaws of the end effector. In another further embodiment, the activating mechanism further comprises an actuator operatively coupled to the transmission link and operable to pivot the transmission link between the first and second positions. In another further embodiment, the robotic surgical tool further includes a spline extending between the first and second ends, the drive gear being movably coupled to the spline and rotatable with rotation of the spline, a drive input arranged at the first end and operatively coupled to the spline such that rotation of the drive input correspondingly rotates the spline and the drive gear, and an instrument driver arranged at an end of a robotic arm and matable with the drive housing at the first end, the instrument driver providing a drive output matable with the drive input such that rotation of the drive output correspondingly rotates the drive input and thereby actuates the activating mechanism. In another further embodiment, the end effector is selected from the group consisting of a surgical stapler, a tissue grasper, surgical scissors, an advanced energy vessel sealer, a clip applier, a needle driver, a babcock including a pair of opposed grasping jaws, bipolar jaws, a suction irrigator, an endoscope, a laparoscope, a probe, a scope, an advanced imaging system, and any combination thereof.

Embodiments of the present disclosure also include a method that includes locating a robotic surgical tool adjacent a patient, the robotic surgical tool comprising a drive housing having a first end, a second end, and a carriage movably mounted to the drive housing, an elongate shaft extending from the carriage and penetrating the first end, the shaft having an end effector arranged at a distal end thereof, and an activating mechanism secured to the carriage and including a transmission link pivotably coupled to the carriage, a transmission drive gear rotatably mounted to a transmission link, a drive gear rotatably mounted to the carriage and operatively coupled to the transmission drive gear, and a transmission driven gear rotatably mounted to the transmission link. The method further includes pivoting the transmission link between a first position, where the transmission driven gear is arranged to actuate the activating mechanism to perform a first function of the end effector, and a second position, where the transmission driven gear is arranged to actuate the activating mechanism to perform a second function of the end effector different from the first function, and actuating the drive gear to rotate the transmission drive gear and thereby drive the driven gear to perform the first or second function. In a further embodiment, actuating the drive gear comprises operating a motor mounted to the carriage, the drive gear being operatively coupled to the motor, providing electrical power to the motor with a power source communicably coupled to the motor, receiving signals that control operation of the motor at a receiver, and regulating operation of the motor based on the signals received from the receiver with an internal processor communicably coupled to the motor, the power source, and the receiver. In another further embodiment, the power source is an internal power source mounted to the carriage, the method further comprising carrying the power source with the carriage as the carriage moves longitudinally. In another further embodiment, the activating mechanism further comprises a spline extending between the first and second ends, a pinion gear movably coupled to the spline and rotatable with rotation of the spline, and a rack gear pivotably coupled to the transmission link and positioned to engage the pinion gear, and wherein pivoting the transmission link between the first and second positions comprises rotating the spline and thereby rotating the pinion gear to drive the rack gear to pivot the transmission link between the first and second positions. In another further embodiment, the robotic surgical tool further comprises a firing rod extending within the shaft and defining external threads, and a knife located at the end effector and operatively coupled to the firing rod, and wherein actuating the drive gear comprises rotating the transmission driven gear in the first position and thereby driving the firing rod at the external threads, and moving the firing rod and the knife longitudinally as the transmission driven gear rotates. In another further embodiment, the shaft comprises a closure tube that defines external threads, and wherein actuating the drive gear comprises rotating the transmission driven gear in the first position and thereby driving the closure tube at the external threads, and moving the closure gear axially along a longitudinal axis of the shaft and thereby closing or opening jaws of the end effector. In another further embodiment, pivoting the transmission link between the first and second positions comprises operating an actuator operatively coupled to the transmission link, the actuator being operatively coupled to the transmission link. In another further embodiment, the activating mechanism further a spline extending between the first and second ends, the drive gear being movably coupled to the spline and rotatable with rotation of the spline, and wherein actuating the drive gear comprises rotating the spline and thereby rotating the drive gear.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
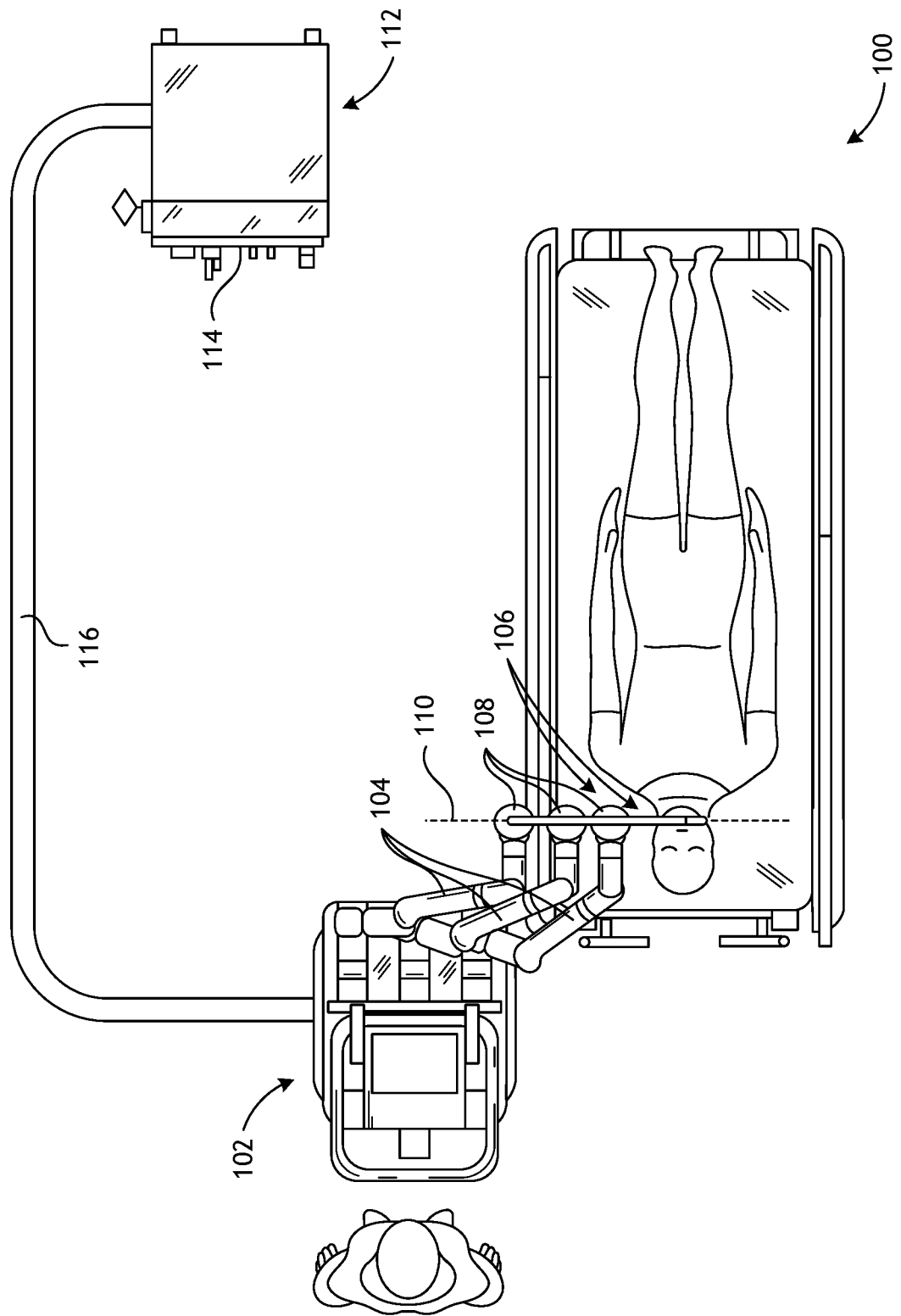
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or re-positioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
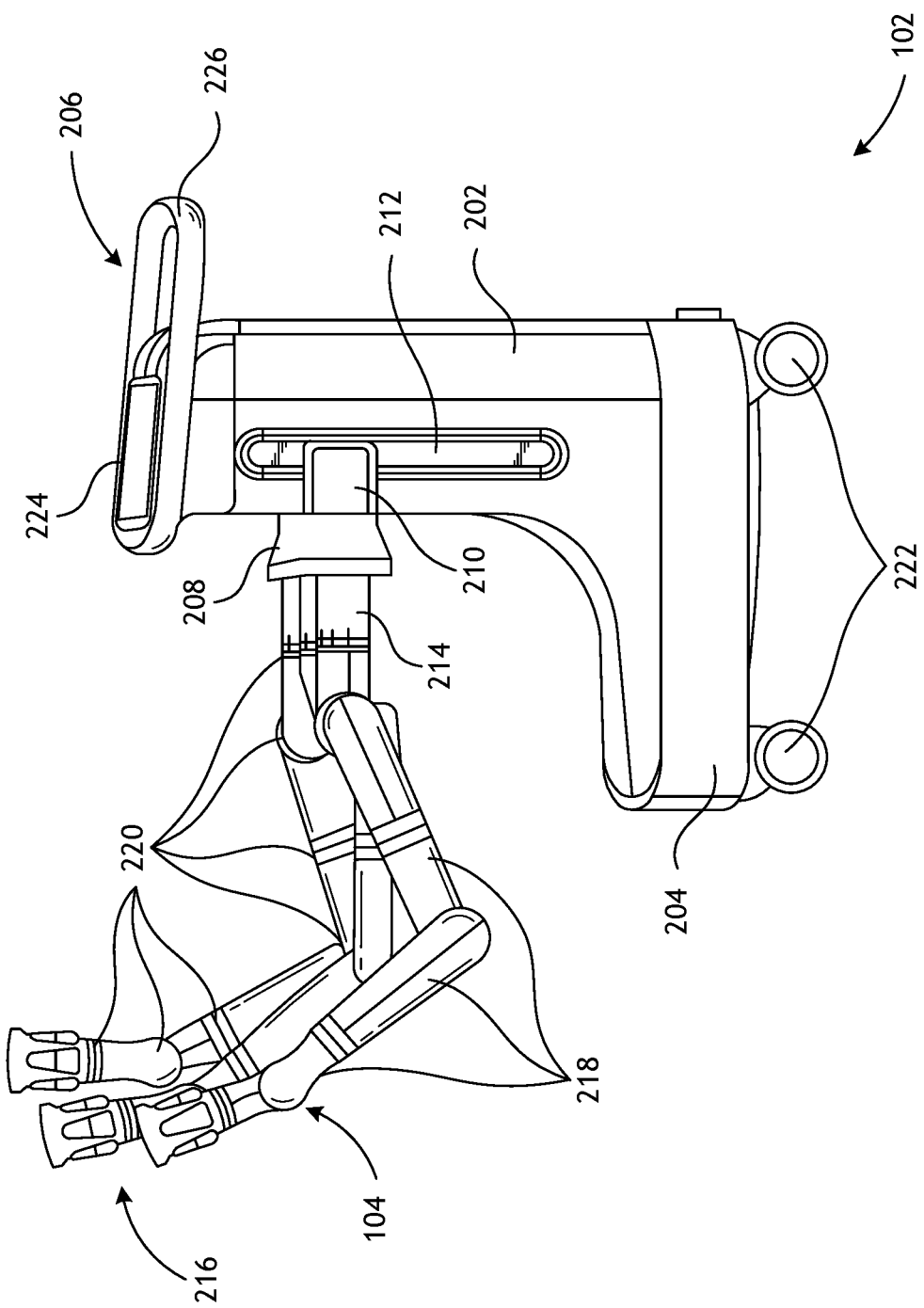
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, that are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, carriage 208, and arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
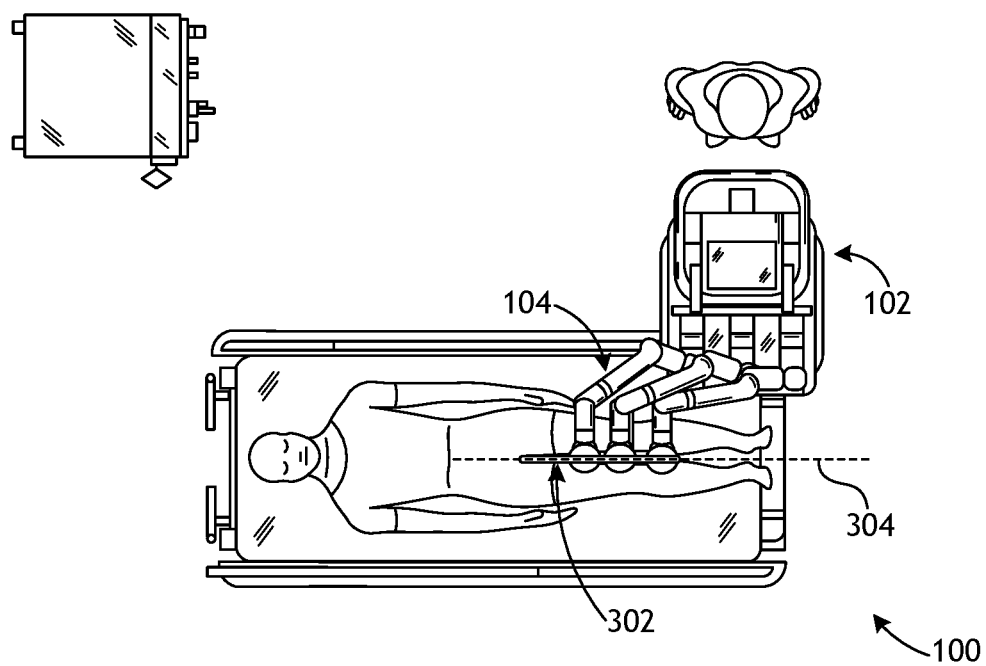
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
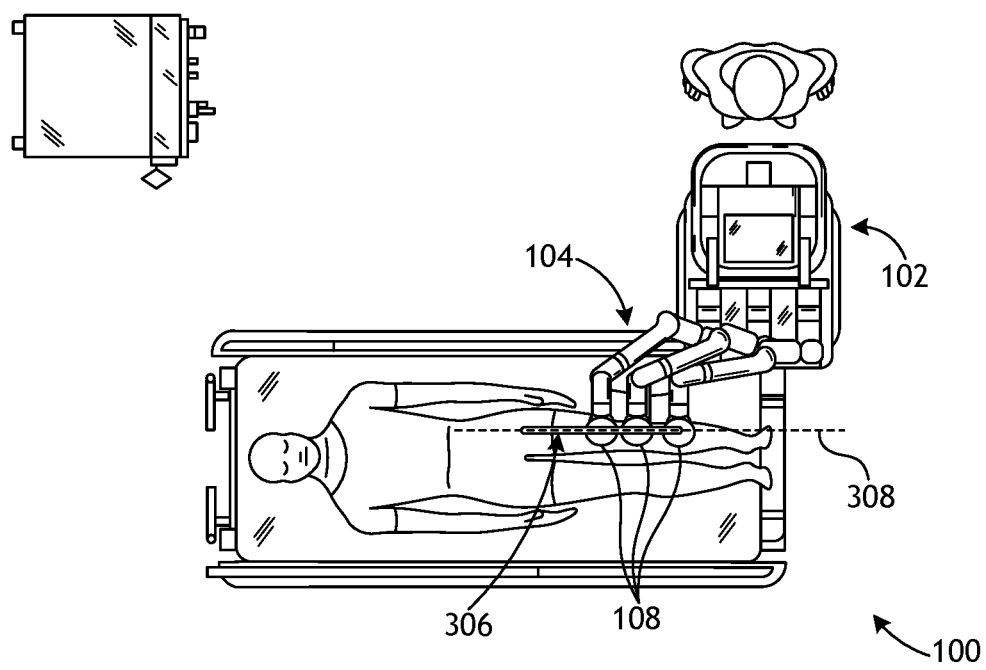
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
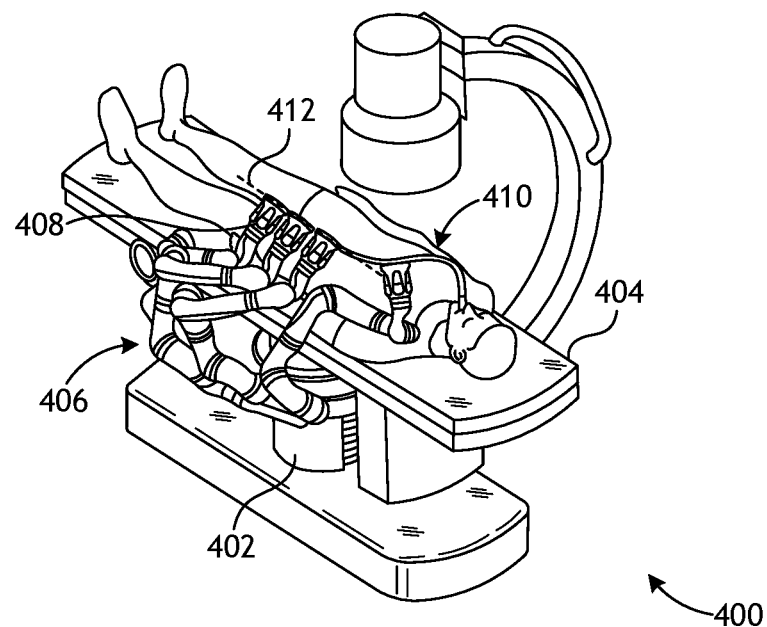
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
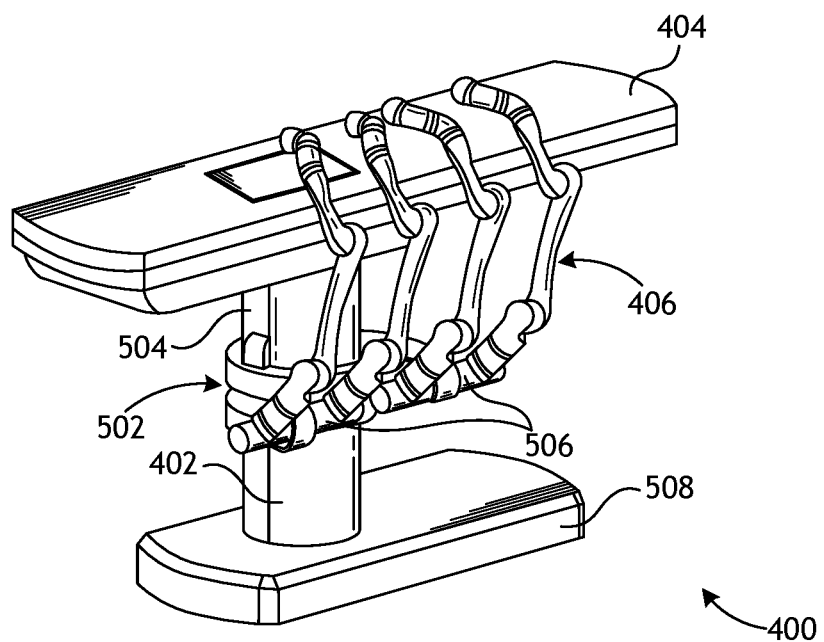
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
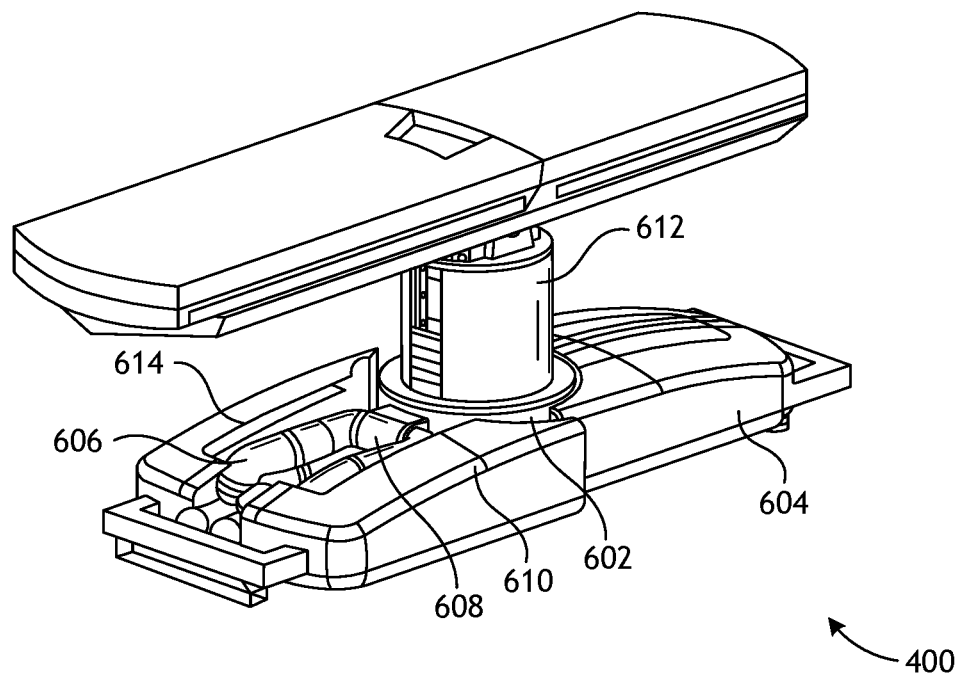
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
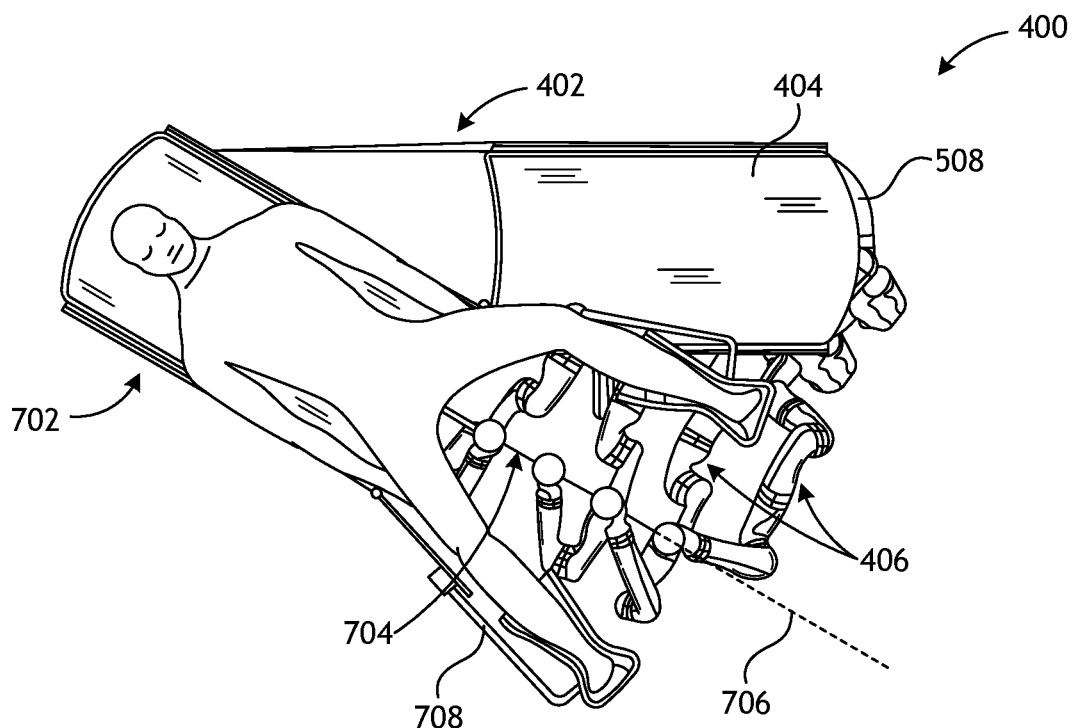
FIG. 7A illustrates an embodiment of a table-based robotic system configured for a ureteroscopy procedure.
Figure 7B:
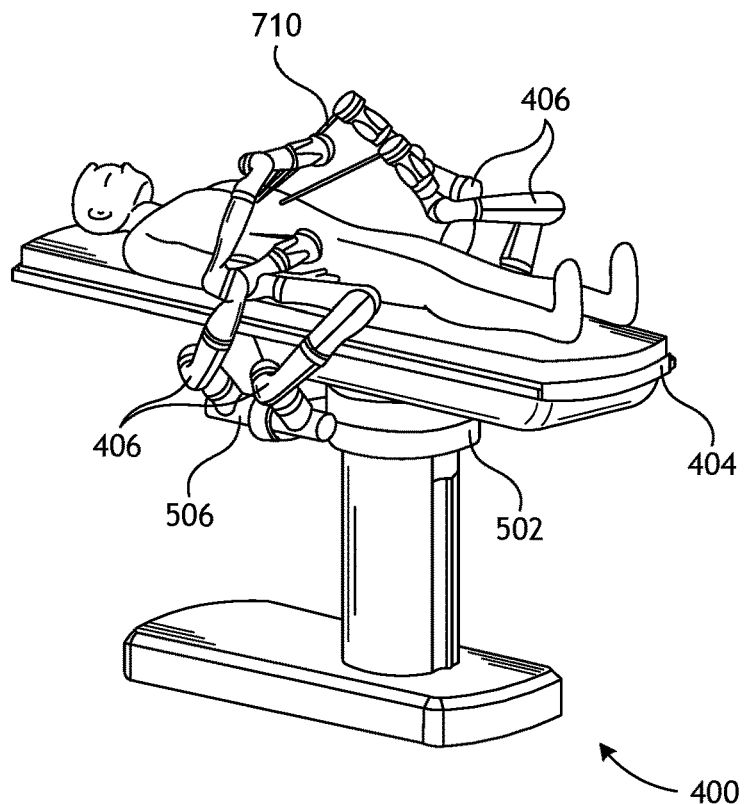
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
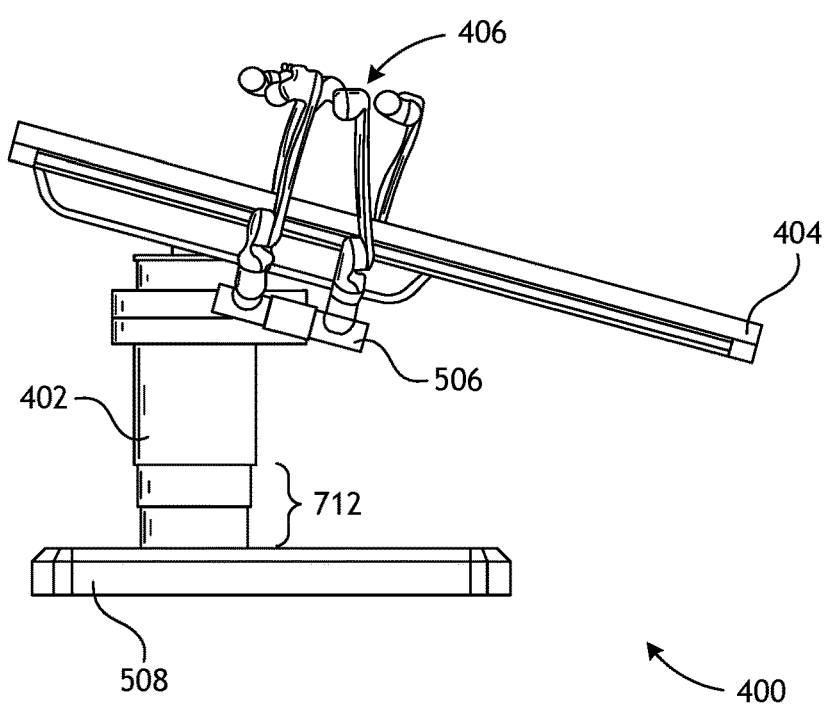
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
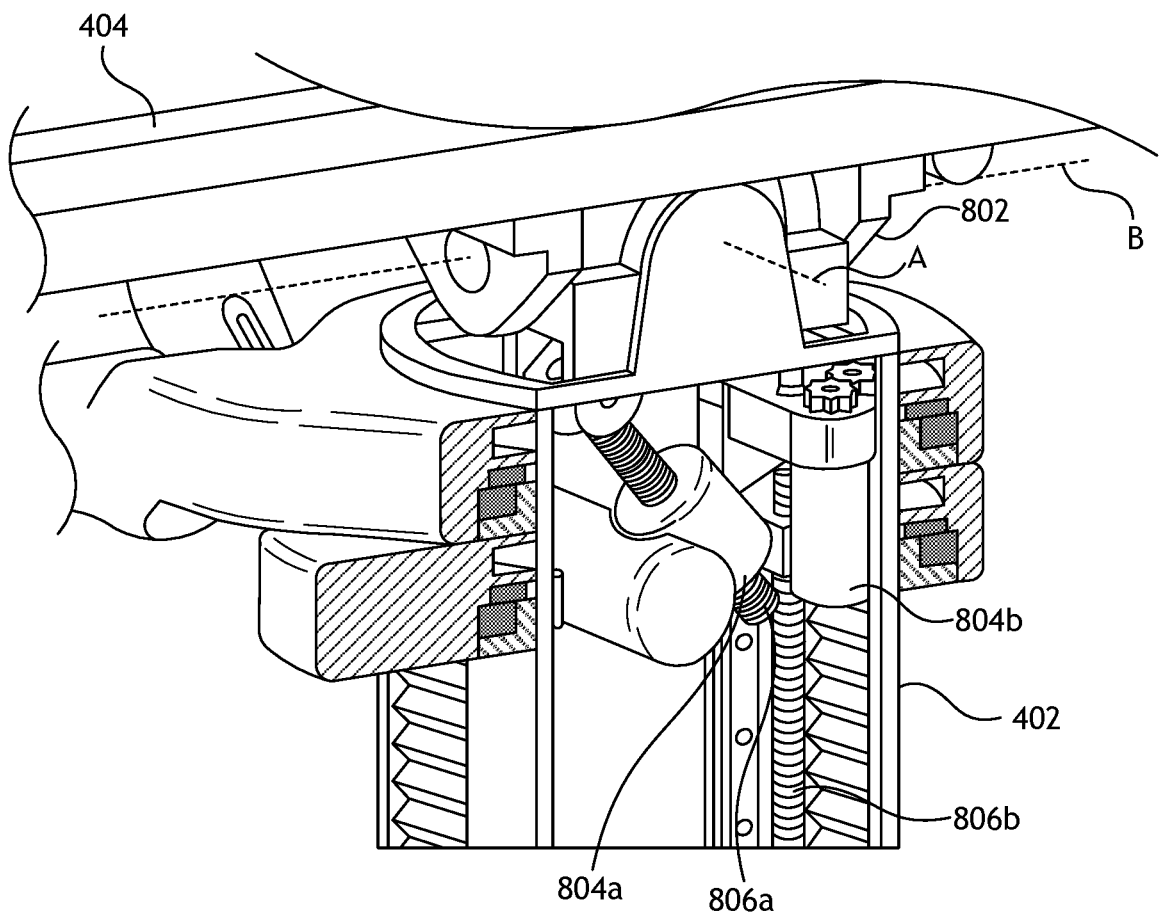
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
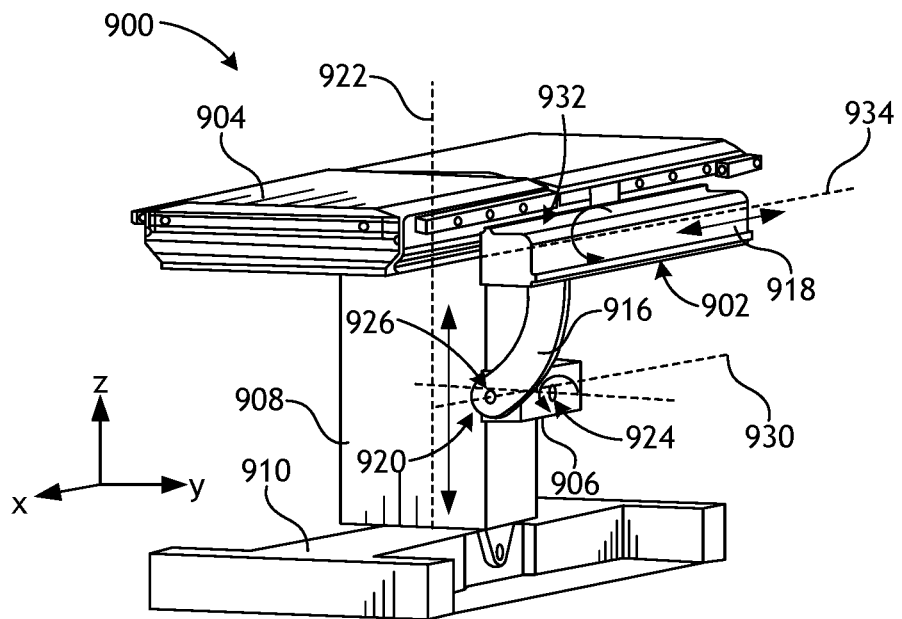
FIG. 9A illustrates an alternative embodiment of a table-based robotic system.
Figure 9B:
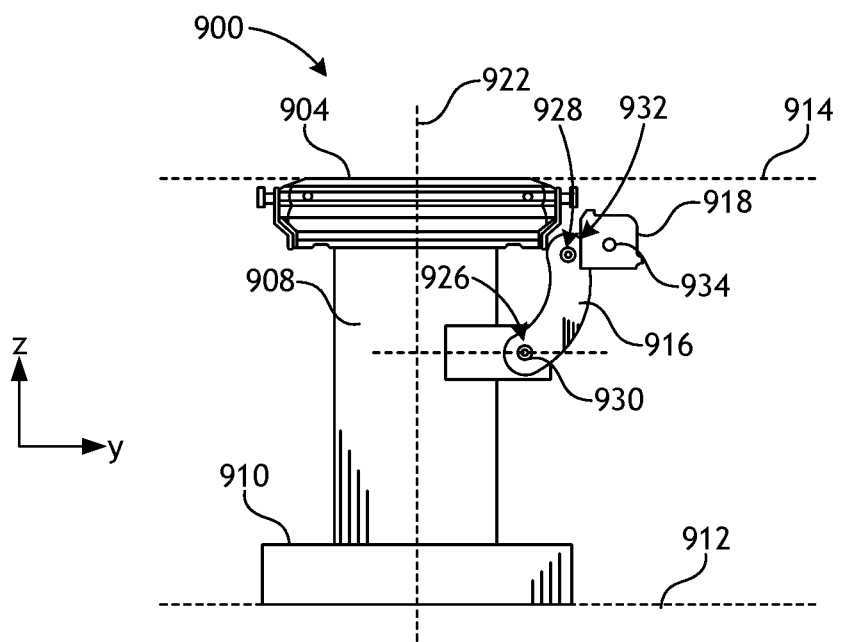
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
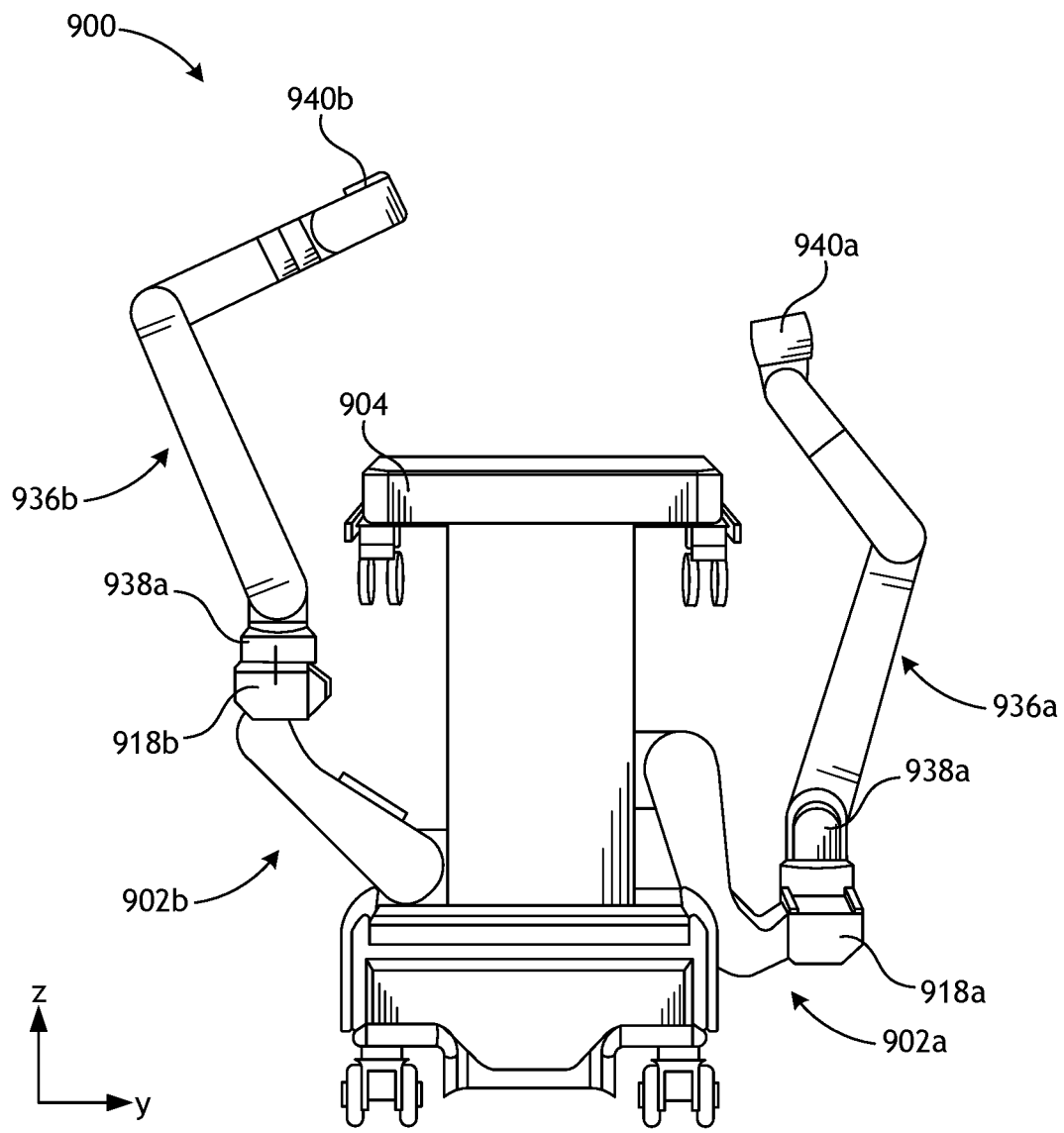
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electromechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
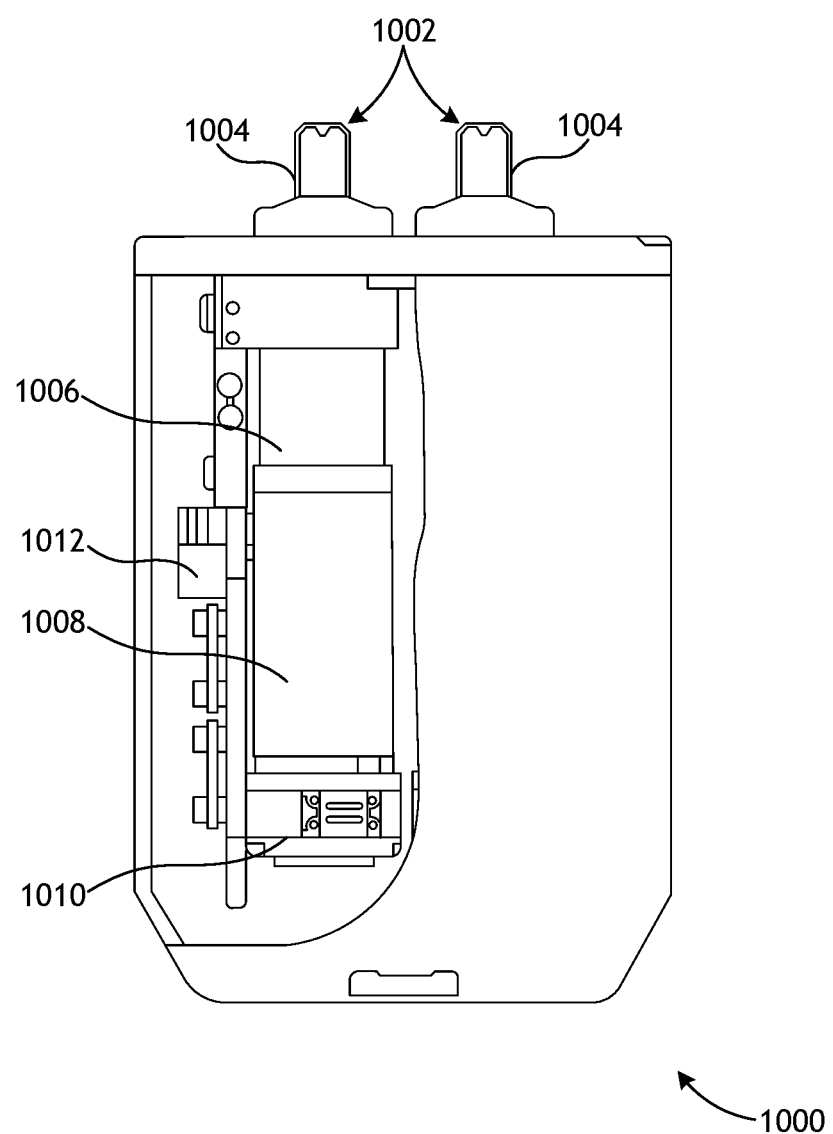
FIG. 10 illustrates an exemplary instrument driver.

FIG. 10 illustrates an example instrument driver 1000, according to one or more embodiments. Positioned at the distal end of a robotic arm, the instrument driver 1000 comprises of one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independent controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
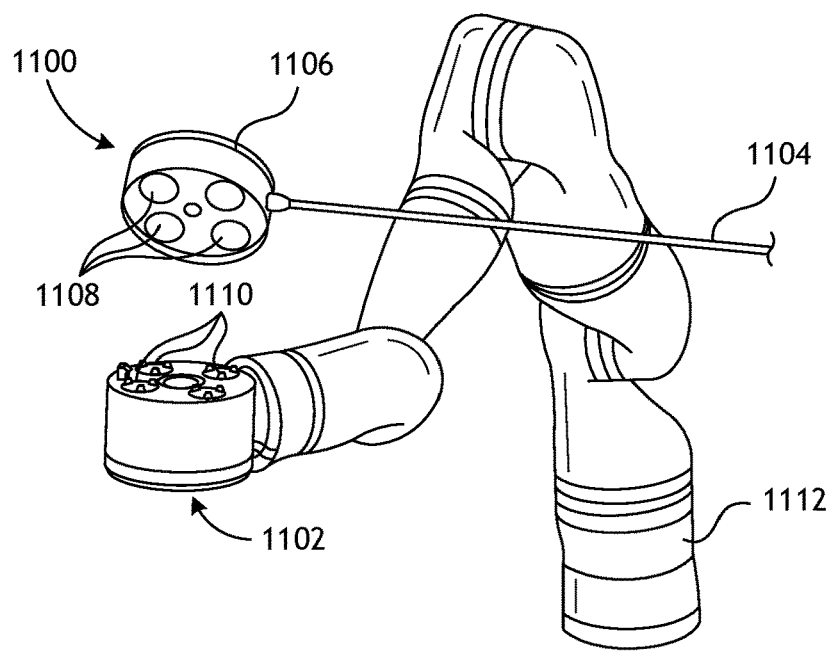
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise of a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
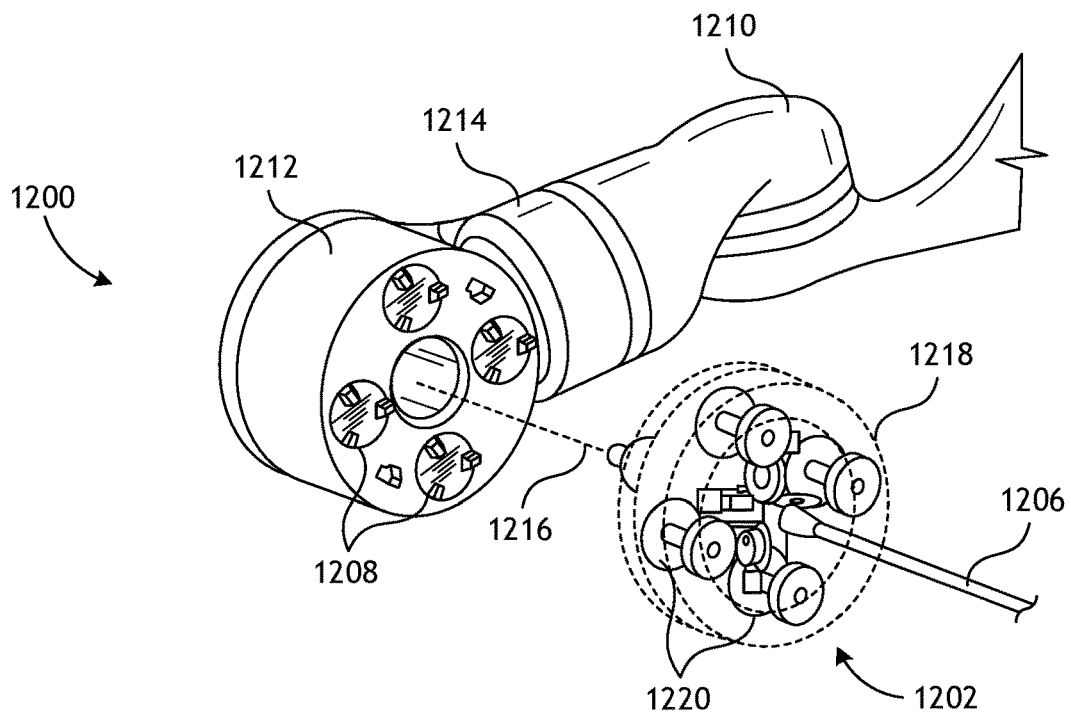
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
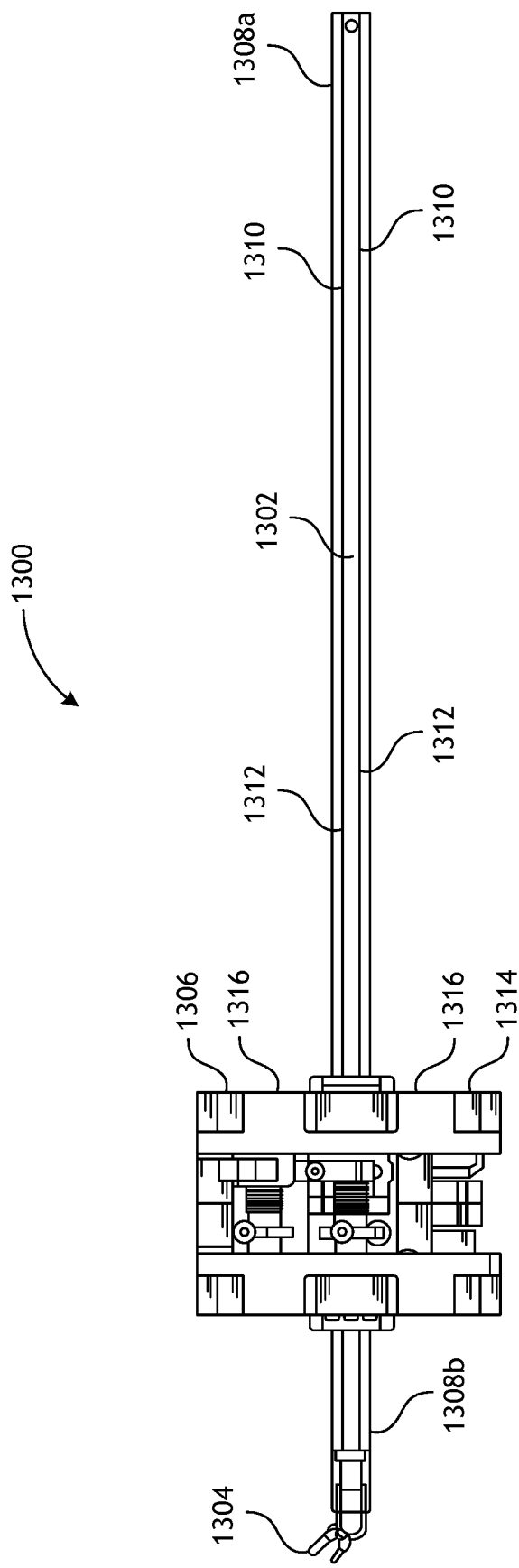
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
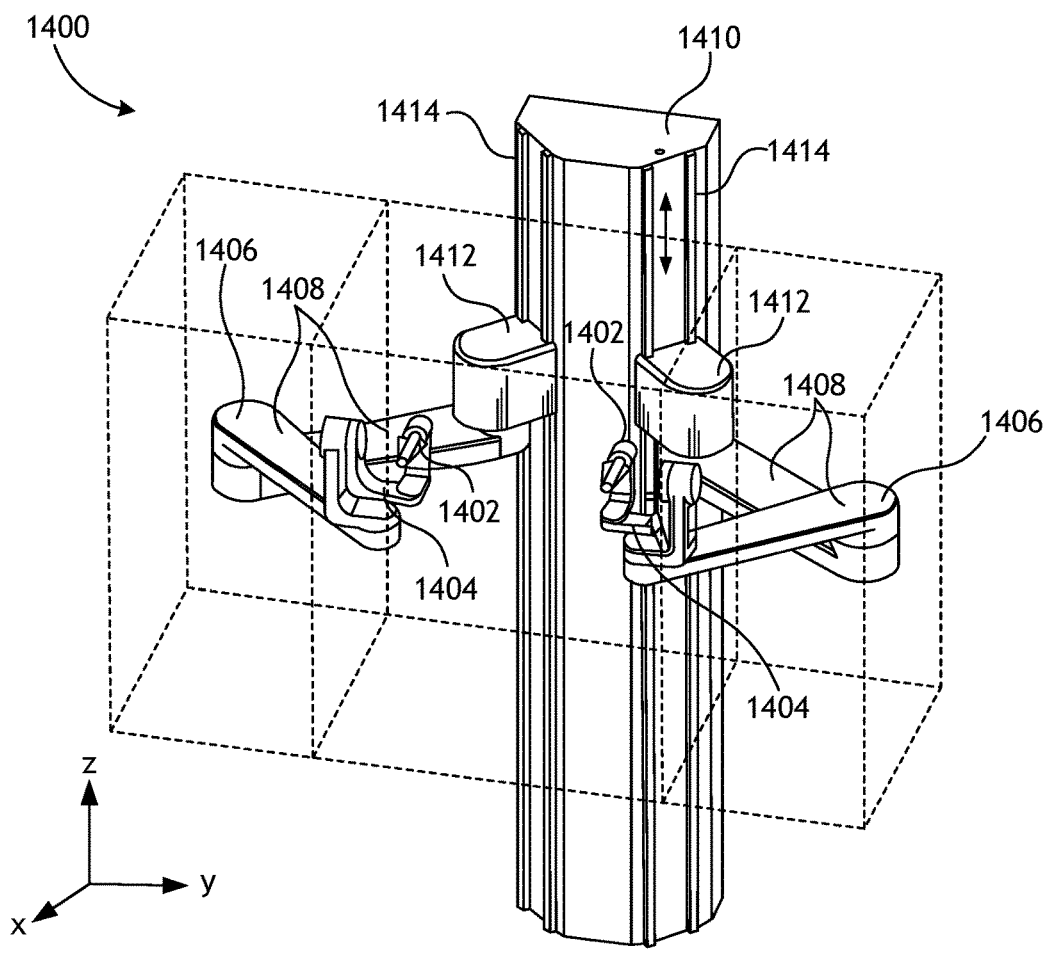
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
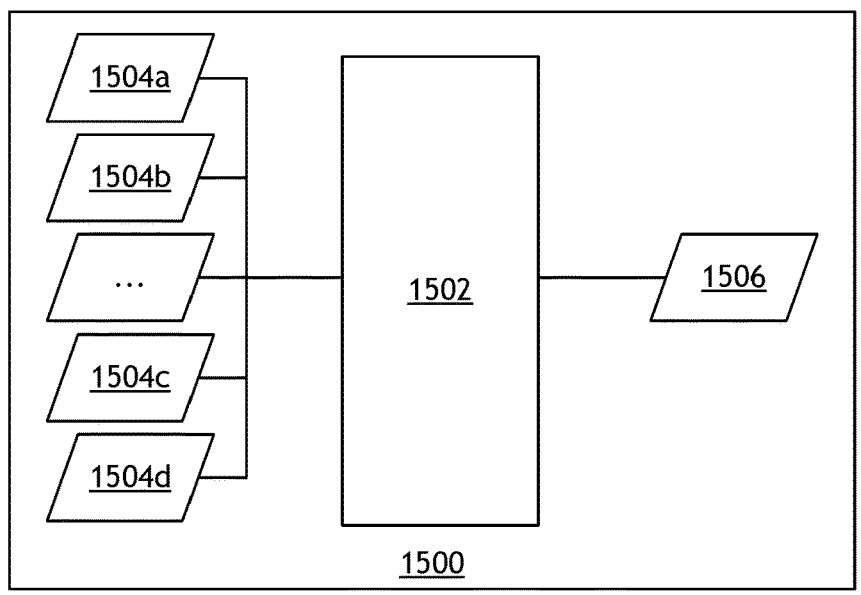
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504*c*. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504*d* may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504*a-d* in combination(s). In some cases, such a combination may use a probabilistic approach where the localization module 1502 assigns a confidence weight to the location determined from each of the input data 1504*a-d*. Thus, where the EM data 1504*c* may not be reliable (as may be the case where there is EM interference) the confidence of the location determined by the EM data 1504*c* can be decrease and the localization module 1502 may rely more heavily on the vision data 1504*b* and/or the robotic command and kinematics data 1504*d*.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the naviga-tional and localization data, such as the position of the instrument within the global coordinate system, anatomical map, etc.

2. Introduction

Embodiments of this disclosure relate to systems and techniques for operating a robotic surgical tool. One robotic surgical tool includes a drive housing having a first end, a second end, and a carriage movably mounted to the drive housing. An elongate shaft extends from the carriage and penetrates the first end, and the shaft has an end effector arranged at a distal end thereof. An activating mechanism is secured to the carriage and includes a transmission link pivotably coupled to the carriage, a transmission drive gear rotatably mounted to a transmission link, and a drive gear rotatably mounted to the carriage and operatively coupled to the transmission drive gear such that rotation of the drive gear correspondingly rotates the transmission drive gear. A transmission driven gear is rotatably mounted to the transmission link and driven by rotation of the transmission drive gear such that the transmission link is pivotable between a first position, where the transmission driven gear is arranged to actuate the activating mechanism to perform a first function of the end effector, and a second position, where the transmission driven gear is arranged to actuate the activating mechanism to perform a second function of the end effector different from the first function. Accordingly, pivoting the transmission driven gear between the first and second positions allows the robotic surgical tool to operate two or more functions of the robotic surgical tool, such as moving the carriage in z-axis translation or actuating an end effector coupled at a distal end of the surgical tool.

3. Description

Figure 16:
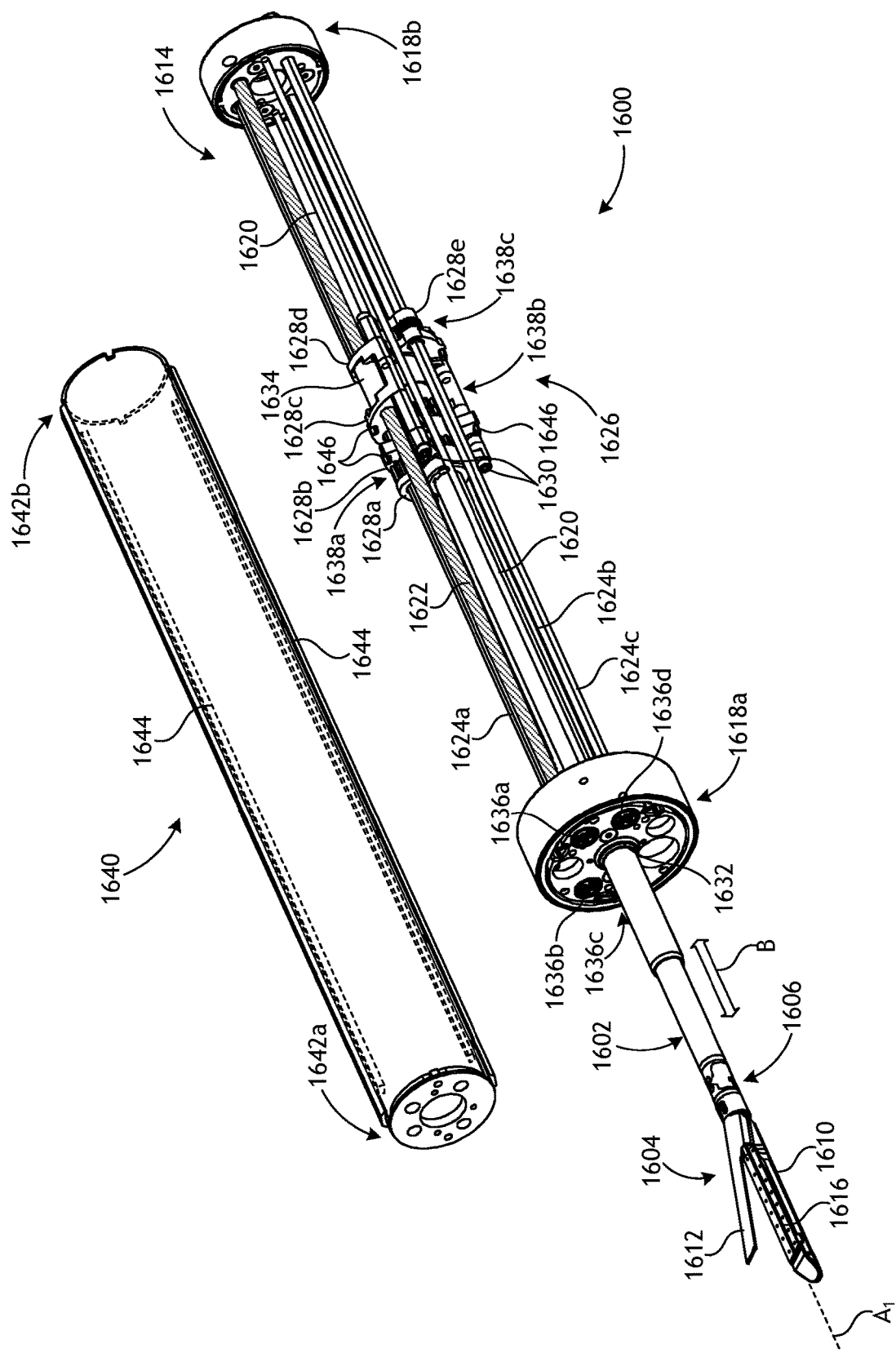
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the medical instruments described above with reference to FIGS. 11-13 and, therefore, may be used in conjunction with a robotic surgical system, such as the robotically-enabled systems 100, 400, and 900 of FIGS. 1-13. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to cut and staple (fasten) tissue. As illustrated, the end effector 1604 includes opposing jaws 1610, 1612 configured to move (articulate) between open and closed positions. Alternatively, the end effector 1604 may comprise other types of instruments requiring opposing jaws such as, but not limited to, tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods. Such end effectors or instruments include, but are not limited to, a suction irrigator, an endoscope (e.g., a camera), a probe, a scope, an advanced imaging system, or any combination thereof.

One or both of the jaws 1610, 1612 may be configured to pivot to actuate the end effector 1604 between open and closed positions. In the illustrated example, the second jaw 1612 is rotatable (pivotable) relative to the first jaw 1610 to move between an open, unclamped position and a closed, clamped position. In other embodiments, however, the first jaw 1610 may move (rotate) relative to the second jaw 1612, without departing from the scope of the disclosure. In yet other embodiments, both jaws 1610, 1612 may move to actuate the end effector 1604 between open and closed positions.

In the illustrated example, the first jaw 1610 is referred to as a "cartridge" or "channel" jaw, and the second jaw 1612 is referred to as an "anvil" jaw. The first jaw 1610 may include a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

In the illustrated embodiment, the pivoting motion at the wrist 1606 is limited to movement in a single plane, e.g., only yaw movement relative to the longitudinal axis $A_1$. The end effector 1604 is depicted in FIG. 16 in the unarticulated position where the longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing 1614 that houses an actuation system designed to facilitate articulation of the wrist 1606 and actuation (operation) of the end effector 1604 (e.g., clamping, firing, rotation, articulation, energy delivery, etc.). The drive housing 1614, alternately referred to as a "stage", provides various coupling features that releasably couple the surgical tool 1600 to an instrument driver of a robotic surgical system, as described in more detail below.

The drive housing 1614 includes a plurality of drive members (obscured in FIG. 16) that extend to the wrist 1606 and the end effector 1604. Selective actuation of one or more of the drive members causes the end effector 1604 to articulate (pivot) relative to the shaft 1602 at the wrist 1606. Selective actuation of one or more other drive members causes the end effector 1604 to actuate (operate). Actuating the end effector 1604 may include closing and/or opening the jaws, 1610, 1612, and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot 1616 defined in the first jaw 1610. As it moves distally, the cutting element transects any tissue grasped between the opposing jaws 1610, 1612. Moreover, as the cutting element advances distally, a plurality of staples contained within the staple cartridge (e.g., housed within the first jaw 1610) are urged (cammed) into deforming contact with corresponding anvil surfaces (e.g., pockets) provided on the second jaw 1612. The deployed staples may form multiple rows of staples that seal opposing sides of the transected tissue.

As illustrated, the drive housing 1614 has a first or "distal" end 1618a and a second or "proximal" end 1618b opposite the first end 1618a. The first end 1618a is alternately referred to as a "handle." In some embodiments, one or more struts 1620 (two shown) extend longitudinally between the first and second ends 1618a,b to help fix the distance between the first and second ends 1618a,b and provide structural stability to the drive housing 1614, and secure the first end 1618a to the second end 1618b. In other embodiments, however, the struts 1620 may be omitted, without departing from the scope of the disclosure.

The drive housing 1614 may also include a lead screw 1622 and one or more splines 1624, which also extend longitudinally between the first and second ends 1618a,b. In the illustrated embodiment, the drive housing 1614 includes a first spline 1624a, a second spline 1624b, and a third spline 1624c. While three splines 1624a-c are depicted in the drive housing 1614, more or less than three may be included, without departing from the scope of the disclosure. Unlike the struts 1620, the lead screw 1622 and the splines 1624a-c are rotatably mounted to the first and second ends 1618a,b. As described in more detail below, selective rotation of the lead screw 1622 and the splines 1624a-c causes various functions of the drive housing 1614 to transpire, such as translating the end effector 1604 along the longitudinal axis $A_1$ (e.g., z-axis translation) causing the end effector 1604 to articulate (pivot) at the wrist 1606, causing the jaws 1610, 1612 to open and close, and causing the end effector 1604 to fire (operate).

The drive housing 1614 further includes a carriage 1626 movably mounted along the lead screw 1622 and the splines 1624a-c and housing various activating mechanisms configured to cause operation of specific functions of the end effector 1604. The carriage 1626 may comprise two or more layers, shown in FIG. 16 as a first layer 1628a, a second layer 1628b, a third layer 1628c, a fourth layer 1628d, and a fifth layer 1628e. The lead screw 1622 and the splines 1624a-c each extend through portions of one or more of the layers 1628a-e to allow the carriage 1626 to translate along the longitudinal axis $A_1$ with respect to the lead screw 1622 and the splines 1624a-c. In some embodiments, the layers 1628a-e may be secured to each other in series using one or more mechanical fasteners 1630 (two visible) extending between the first layer 1628a and the fifth layer 1628e and through coaxially aligned holes defined in some or all of the layers 1628a-e. While five layers 1628a-e are depicted, more or less than five may be included in the carriage 1626, without departing from the scope of the disclosure.

The shaft 1602 is coupled to and extends distally from the carriage 1626 through the first end 1618a of the drive housing 1614. In the illustrated embodiment, for example, the shaft 1602 penetrates the first end 1618a at a central aperture 1632 defined through the first end 1618a. The carriage 1626 is movable between the first and second ends 1618a,b along the longitudinal axis $A_1$ (e.g., z-axis translation) and is thereby able to advance or retract the end effector 1604 relative to the drive housing 1614, as indicated by the arrows B. More specifically, in some embodiments, the carriage 1626 includes a carriage nut 1634 mounted to the lead screw 1622 and secured between the third and fourth layers 1628c,d. The outer surface of the lead screw 1622 defines outer helical threading and the carriage nut 1634 defines corresponding internal helical threading (not shown) matable with the outer helical threading of the lead screw 1622. As a result, rotation of the lead screw 1622 causes the carriage nut 1634 to advance or retract the carriage 1626 along the longitudinal axis $A_1$ and correspondingly advance or retract the end effector 1604 relative to the drive housing 1614.

As indicated above, the lead screw 1622 and the splines 1624a-c are rotatably mounted to the first and second ends 1618a,b. More specifically, the first end 1618a of the drive housing 1614 may include one or more rotatable drive inputs actuatable to independently drive (rotate) the lead screw 1622 and the splines 1624a-c. In the illustrated embodiment, the drive housing 1614 includes a first drive input 1636a, a second drive input 1636b, a third drive input 1636c (occluded by the shaft 1602, see FIG. 17B), and a fourth drive input 1636d. As described below, each drive input 1636a-d may be matable with a corresponding drive output of an instrument driver such that movement (rotation) of a given drive output correspondingly moves (rotates) the associated drive input 1636a-d and thereby rotates the mated lead screw 1622 or spline 1624a-c. While only four drive inputs 1636a-d are depicted, more or less than four may be included in the drive housing 1614, depending on the application.

The first drive input 1636a may be operatively coupled to the lead screw 1622 such that rotation of the first drive input 1636a correspondingly rotates the lead screw 1622, which causes the carriage nut 1634 and the carriage 1626 to advance or retract along the longitudinal axis $A_1$, depending on the rotational direction of the lead screw 1622. As used herein the phrase "operatively coupled" refers to a coupled engagement, either directly or indirectly, where movement of one component causes corresponding movement of another component. With respect to the first drive input 1636a being operatively coupled to the lead screw 1622, such operative coupling may be facilitated through intermeshed gears (not shown) arranged within the second end 1618a, but could alternatively be facilitated through other mechanical means, such as cables, pulleys, drive rods, direct couplings, etc., without departing from the scope of the disclosure.

The second drive input 1636b may be operatively coupled to the first spline 1624a such that rotation of the second drive input 1636b correspondingly rotates the first spline 1624a. In some embodiments, the first spline 1624a may be operatively coupled to a first activating mechanism 1638a of the carriage 1626, and the first activating mechanism 1638a may be operable to open and close the jaws 1610, 1612. Accordingly, rotating the second drive input 1636b will correspondingly actuate the first activating mechanism 1638a and thereby open or close the jaws 1610, 1612, depending on the rotational direction of the first spline 1624a.

The third drive input 1636c may be operatively coupled to the second spline 1624b such that rotation of the third drive input 1636c correspondingly rotates the second spline 1624b. In some embodiments, the second spline 1624b may be operatively coupled to a second activating mechanism 1638b of the carriage 1626, and the second activating mechanism 1638b may be operable to articulate the end effector 1604 at the wrist 1606. Accordingly, rotating the third drive input 1636c will correspondingly actuate the second activating mechanism 1638b and thereby cause the wrist 1606 to articulate in at least one degree of freedom, depending on the rotational direction of the second spline 1624b.

The fourth drive input 1636d may be operatively coupled to the third spline 1624c such that rotation of the fourth drive input 1636d correspondingly rotates the third spline 1624c. In some embodiments, the third spline 1624c may be operatively coupled to a third activating mechanism 1638c of the carriage 1626, and the third activating mechanism 1638c may be operable to fire the cutting element (knife) at the end effector 1604. Accordingly, rotating the fourth drive input 1636d will correspondingly actuate the third activating mechanism 1638c and thereby cause the knife to advance or retract, depending on the rotational direction of the third spline 1624c.

In the illustrated embodiment, and as described in more detail below, the activating mechanisms 1638a-c comprise intermeshed gearing assemblies including one or more drive gears driven by rotation of the corresponding spline 1624a-c and configured to drive one or more corresponding driven gears that cause operation of specific functions of the end effector 1604.

In some embodiments, the drive housing 1614 may include a shroud 1640 sized to receive and otherwise surround the carriage 1626, the lead screw 1622, and the splines 1624a-c. In the illustrated embodiment, the shroud 1640 comprises a tubular or cylindrical structure having a first end 1642a matable with the first end 1618a of the drive housing 1614, and a second end 1642b matable with the second end 1618b of the drive housing 1614. The carriage 1626, the lead screw 1622, and the splines 1624a-c can all be accommodated within the interior of the shroud 1640, and the carriage 1626 may engage and traverse (ride on) one or more rails 1644 (shown in phantom) fixed to the shroud 1640. The rails 1644 extend longitudinally and parallel to the lead screw 1622 and are sized to be received within corresponding notches 1646 defined on the outer periphery of the carriage 1626 and, more particularly, on the outer periphery of one or more of the carriage layers 1628a-e. As the carriage 1626 translates along the longitudinal axis $A_1$, the rails 1644 help maintain the angular position of the carriage 1626 and assume any torsional loading that might otherwise adversely affect movement or operation of the carriage 1626.

Figure 17A:
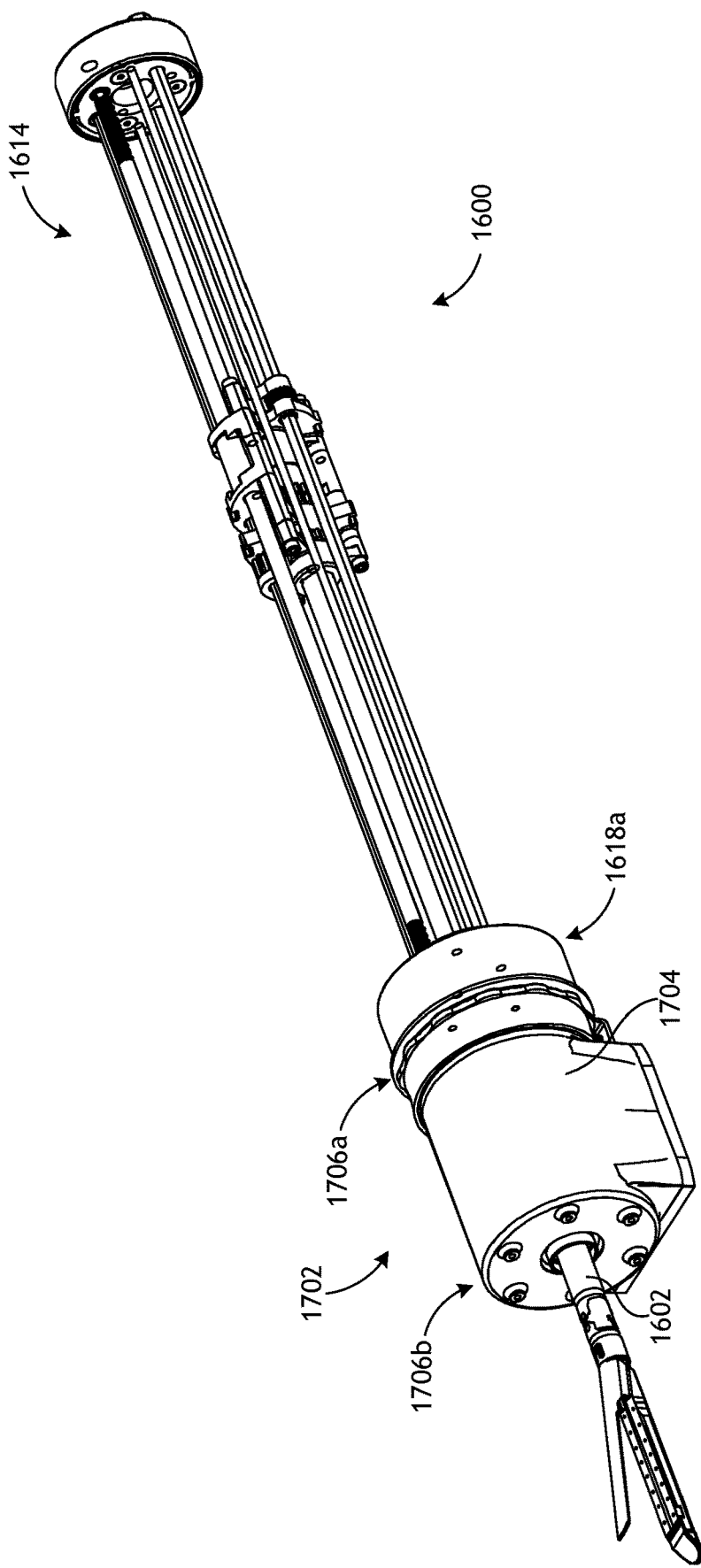
FIG. 17A is an isometric view of the surgical tool of FIG. 16 releasably coupled to an example instrument driver, according to one or more embodiments.

FIG. 17A is an isometric view of the surgical tool 1600 of FIG. 16 releasably coupled to an example instrument driver 1702, according to one or more embodiments. The instrument driver 1702 may be similar in some respects to the instrument drivers 1102, 1200 of FIGS. 11 and 12, respectively, and therefore may be best understood with reference thereto. Similar to the instrument drivers 1102, 1200, for example, the instrument driver 1702 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1702.

The instrument driver 1702 has a body 1704 having a first or "proximal" end 1706a and a second or "distal" end 1706b opposite the first end 1706a. In the illustrated embodiment, the first end 1706a of the instrument driver 1702 is matable with and releasably coupled to the first end 1618a of the drive housing 1614, and the shaft 1602 of the surgical tool 1602 extends through the body 1704 and distally from the second end 1706b.

Figure 17B:
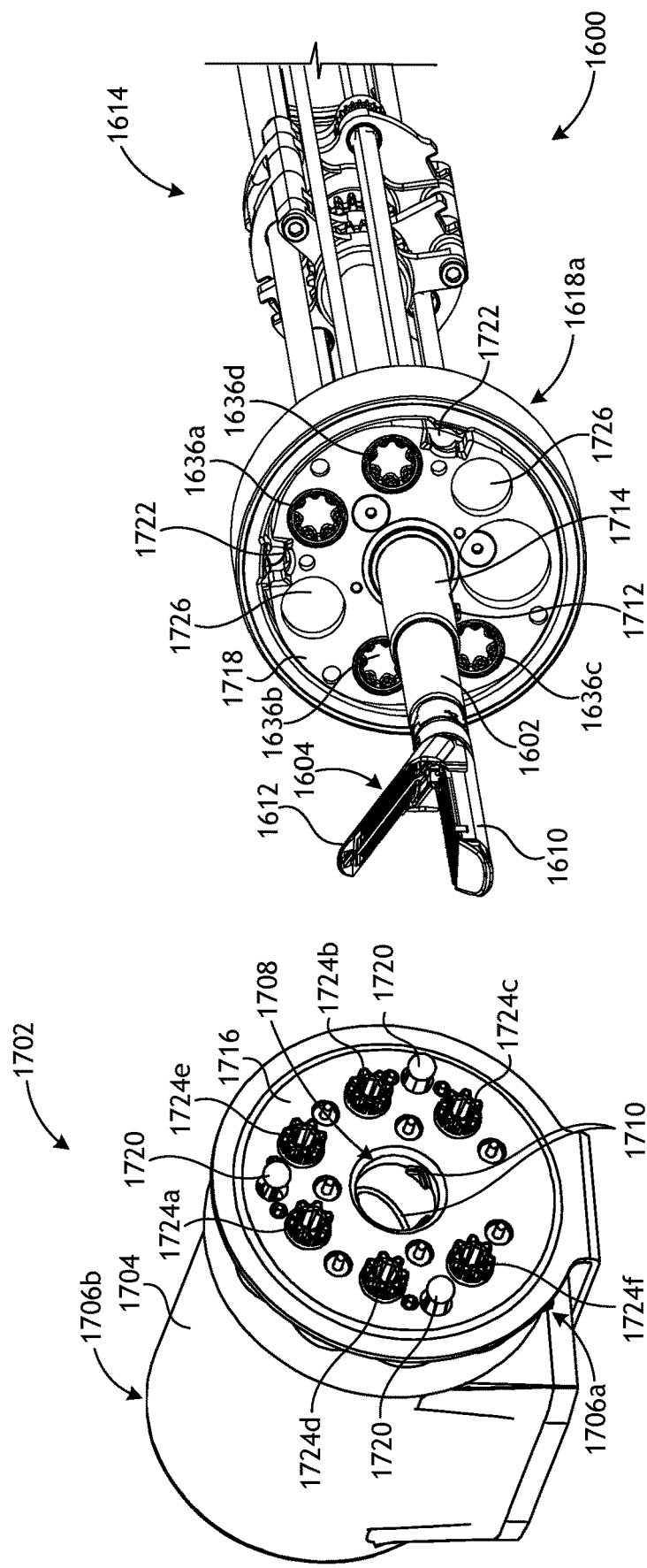
FIG. 17B provides separated isometric end views of the instrument driver and the surgical tool of FIG. 17A.

FIG. 17B depicts separated isometric end views of the instrument driver 1702 and the surgical tool 1600 of FIG. 17A. With the jaws 1610, 1612 closed, the shaft 1602 and the end effector 1604 can penetrate the instrument driver 1702 by extending through a central aperture 1708 defined longitudinally through the body 1704 between the first and second ends 1706a,b. To align the surgical tool 1600 with the instrument driver 1702 in a proper angular orientation, one or more alignment guides 1710 may be provided or otherwise defined within the central aperture 1708 and configured to engage one or more corresponding alignment features 1712 provided on the surgical tool 1600. In the illustrated embodiment, the alignment feature 1712 comprises a protrusion or projection defined on or otherwise provided by an alignment nozzle 1714 extending distally from the first end 1618a of the drive housing 1614. In one or more embodiments, the alignment guide 1710 may comprise a curved or arcuate shoulder or lip configured to receive and guide the alignment feature 1712 as the alignment nozzle 1714 enters the central aperture 1708. As a result, the surgical tool 1600 is oriented to a proper angular alignment with the instrument driver 1702 as the alignment nozzle 1714 is advanced distally through the central aperture 1708. In other embodiments, the alignment nozzle 1714 may be omitted and the alignment feature 1712 may alternatively be provided on the shaft 1602, without departing from the scope of the disclosure.

As illustrated, a drive interface 1716 is provided at the first end 1706a of the instrument driver 1702, and a driven interface 1718 is provided at the first end 1618a of the drive housing 1614. The drive and driven interfaces 1716, 1718 may be configured to mechanically, magnetically, and/or electrically couple the drive housing 1614 to the instrument driver 1702. To accomplish this, the drive and driven interfaces 1716, 1718 may provide one or more matable locating features configured to secure the drive housing 1614 to the instrument driver 1702. In the illustrated embodiment, for example, the drive interface 1716 provides one or more interlocking features 1720 (three shown) configured to locate and mate with one or more complementary-shaped pockets 1722 (two shown, one occluded) provided on the driven interface 1718. In some embodiments, the features 1720 may be configured to align and mate with the pockets 1722 via an interference or snap fit engagement, for example.

The instrument driver 1702 also includes one or more drive outputs that extend through the drive interface 1716 to mate with the drive inputs 1636a-d provided at the first end 1618a of the drive housing 1614. More specifically, the instrument driver 1702 includes a first drive output 1724a matable with the first drive input 1636a, a second drive output 1724b matable with the second drive input 1636b, a third drive output 1724b matable with the third drive input 1636c, and a fourth drive output 1724d matable with the fourth drive input 1636d. In some embodiments, as illustrated, the drive outputs 1724a-d may define splines or features designed to mate with corresponding splined receptacles of the drive inputs 1636a-d. Once properly mated, the drive inputs 1636a-d will share axes of rotation with the corresponding drive outputs 1724a-d to allow the transfer of rotational torque from the drive outputs 1724a-d to the corresponding drive inputs 1636a-d. In some embodiments, each drive output 1724a-d may be spring loaded and otherwise biased to spring outwards away from the drive interface 1716. Each drive output 1724a-d may be capable of partially or fully retracting into the drive interface 1716.

In some embodiments, the instrument driver 1702 may include additional drive outputs, depicted in FIG. 17B as a fifth drive output 1724e and a sixth drive output 1724f. The fifth and sixth drive outputs 1724e,f may be configured to mate with additional drive inputs (not shown) of the drive housing 1614 to help undertake one or more additional functions of the surgical tool 1600. In the illustrated embodiment, however, the drive housing 1614 does not include additional drive inputs matable with the fifth and sixth drive outputs 1724e,f. Instead, the driven interface 1718 defines corresponding recesses 1726 configured to receive the fifth and sixth drive outputs 1724e,f. In other applications, however, fifth and/or sixth drive inputs (not shown) could be included in the drive housing 1614 to mate with the fifth and sixth drive outputs 1724e,f, or the surgical tool 1600 might be replaced with another surgical tool having fifth and/or sixth drive inputs, which would be driven by the fifth and/or sixth drive outputs 1724e,f.

While not shown, in some embodiments, an instrument sterile adapter (ISA) may be placed at the interface between the instrument driver 1702 and the surgical tool 1600. In such applications, the interlocking features 1720 may operate as alignment features and possible latches for the ISA to be placed, stabilized, and secured. Stability of the ISA may be accomplished by a nose cone feature provided by the ISA and extending into the central aperture 1708 of the instrument driver 1702. Latching can occur either with the interlocking features 1720 or at other locations at the interface. In some cases, the ISA will provide the means to help align and facilitate the latching of the surgical tool 1600 to the ISA and simultaneously to the instrument driver 1702.

Firing with Embedded Motor on Translating Carriage

Figure 18:
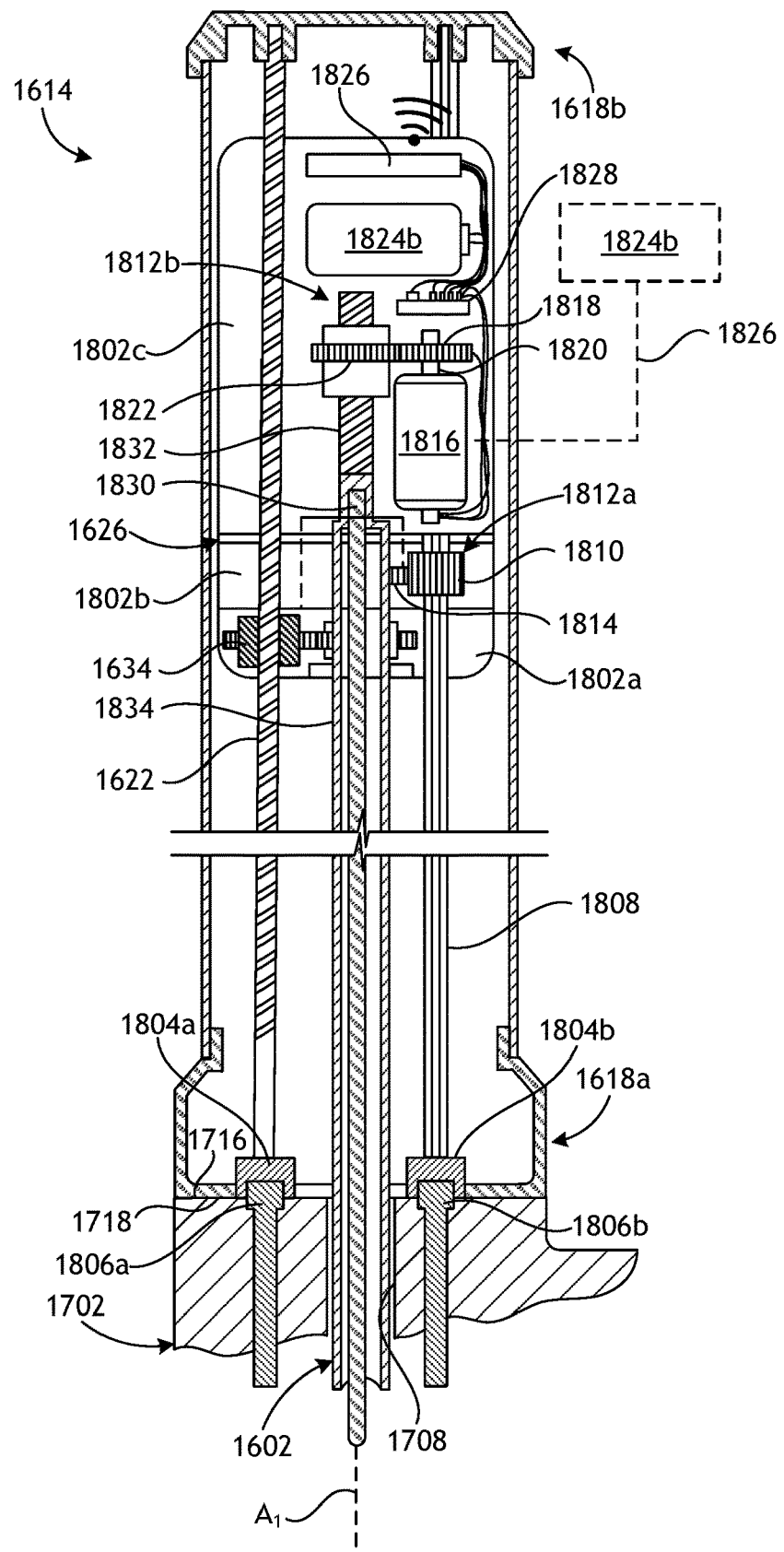
FIG. 18 is a partial cross-sectional side view of another example of the drive housing of FIG. 16, according to one or more embodiments.

FIG. 18 is a partial cross-sectional side view of another example of the drive housing 1614 of FIG. 16, according to one or more embodiments. As illustrated, the drive housing 1614 includes the first and second ends 1618a,b, and the instrument driver 1702 can be removably coupled to the drive housing 1614 at the first end 1618a (alternately referred to as the "handle"). The lead screw 1622 extends longitudinally between the first and second ends 1618a,b, and the carriage 1626 is movably mounted to the lead screw 1622 at the carriage nut 1634 to allow the carriage 1626 to traverse the lead screw 1622 along the longitudinal axis $A_1$ (i.e., z-axis translation). In the illustrated embodiment, the carriage 1626 includes three structural layers, shown as a first layer 1802a, a second layer 1802b, and a third layer 1802c. The layers 1802a-c may be similar in some respects to the layers 1628a-e of FIG. 16, and thus may house or contain an activating mechanism or otherwise help facilitate one or more functions of the surgical tool 1600 (FIG. 16). While the carriage 1626 in FIG. 18 includes three layers 1802a-c, the carriage 1626 may alternatively include more or less than three layers 1802a-c, without departing from the scope of the disclosure.

The shaft 1602 extends distally from the carriage 1626 through the first end 1618a of the drive housing 1614 and subsequently through the central aperture 1708 of the instrument driver 1702 when mounted thereto. The drive housing 1614 may be releasably coupled to the instrument driver 1702 by extending the shaft 1602 through the central aperture 1708 and mating the drive interface 1716 of the instrument driver 1702 to the driven interface 1718 of the drive housing 1614, as generally described above.

In the illustrated embodiment, the driven interface 1718 of the drive housing 1614 includes a first drive input 1804a and a second drive input 1804b, and the drive interface 1716 includes a first drive output 1806a and a second drive output 1806b. The drive inputs 1804a,b may be substantially similar to the drive inputs 1636a-d of FIGS. 16 and 17B, and the drive outputs 1806a,b may be substantially similar to the drive outputs 1724a-d of FIG. 17B. Accordingly, the drive inputs 1804a,b may be matable with the drive outputs 1806a,b such that movement (rotation) of a given drive output 1806a,b correspondingly moves (rotates) the associated drive input 1804a,b. While only two drive inputs 1804a,b and two drive outputs 1806a,b are depicted, more or less than two may be included in the drive housing 1614, without departing from the scope of the disclosure.

The first drive input 1804a is operatively coupled to the lead screw 1622 such that rotation of the first drive input 1804a (via rotation of the first drive output 1806a) correspondingly rotates the lead screw 1622 in the same angular direction. As the lead screw 1622 rotates, the carriage nut 1634 housed within or otherwise secured to the first layer 1802a is urged to axially traverse the lead screw 1622 and simultaneously advance or retract the carriage 1626 along the longitudinal axis $A_1$, depending on the rotational direction of the lead screw 1622. Moreover, as the carriage 1626 advances or retracts, the shaft 1602 and the end effector 1604 (FIGS. 16 and 17A-17B) arranged at the distal end of the shaft 1602 correspondingly move distally or proximally (i.e., z-axis translation).

The second drive input 1804b is operatively coupled to a spline 1808 such that rotation of the second drive input 1804b (via rotation of the second drive output 1806b) correspondingly rotates the spline 1808 in the same angular direction. The spline 1808 may be similar to the splines 1624a-c of FIG. 16 and, therefore, may extend between and be rotatably mounted to the first and second ends 1618a,b. A drive gear 1810 is movably coupled to the spline 1808 and configured to rotate as the spline 1808 rotates. In some embodiments, the drive gear 1810 may comprise a separate component part disposed about the spline 1808 and capable of translating (sliding) along the spline 1808 as the carriage 1626 moves along the longitudinal axis $A_1$. In other embodiments, however, the spline 1808 may be shaped and otherwise configured to operate as the drive gear 1810 to advantageously reduce the number of component parts.

The spline 1808 is operatively coupled to a first activating mechanism 1812a such that rotating the spline 1808 will correspondingly actuate the first activating mechanism 1812a. In the illustrated embodiment, the first activating mechanism 1812a is housed in or otherwise secured to the carriage 1626 and, more particularly, to the second layer 1802b. The first activating mechanism 1812a may be the same as or similar to the any of the activating mechanisms 1638a-c described herein with reference to FIG. 16. Accordingly, the first activating mechanism 1812a may be operable to carry out one or more functions of the end effector 1604 (FIGS. 16 and 17A-17B), such as opening or closing the jaws 1610, 1612 (FIGS. 16 and 17A-17B), articulating the end effector 1604 at the wrist 1606 (FIG. 16), or advancing or retracting a knife at the end effector 1604. In the illustrated embodiment, actuation of the first activating mechanism 1812a causes the end effector 1604 to articulate.

The drive gear 1810 may be configured to drive a driven gear 1814 also rotatably mounted to the carriage 1626 and forming part of the first activating mechanism 1812a. In some embodiments, as illustrated, the drive gear 1810 may be positioned to directly intermesh with the driven gear 1814 and thereby directly drive the driven gear 1814 as the spline 1808 rotates. In other embodiments, however, one or more idler gears (not shown) may interpose the drive gear 1810 and the driven gear 1814 and may otherwise transfer torque from the drive gear 1810 to the driven gear 1814 via an intermeshed gearing arrangement. The driven gear 1814 may be operatively coupled to one or more mechanical features (omitted for simplicity) of the first activating mechanism 1812a such that rotation of the driven gear 1814 causes the first activating mechanism 1812a to actuate.

A second activating mechanism 1812b may also be included with the carriage 1626. In the illustrated embodiment, the second activating mechanism 1812b is housed within or otherwise secured to the third layer 1802c. Similar to the first activating mechanism 1812a, the second activating mechanism 1812b may be similar in some respects to one or more of the activating mechanisms 1638a-c described herein with reference to FIG. 16. Accordingly, the second activating mechanism 1812b may be operable to carry out one or more functions of the end effector 1604 (FIGS. 16 and 17A-17B), such as opening or closing the jaws 1610, 1612 (FIGS. 16 and 17A-17B), articulating the end effector 1604 at the wrist 1606 (FIG. 16), or advancing or retracting a knife (cutting element) at the end effector 1604.

Unlike the activating mechanisms 1638a-c of FIG. 16, however, the second activating mechanism 1812b is not driven by a spline rotatable by any of the drive inputs 1804a,b or through operation (actuation) of any of the drive outputs 1806a,b of the instrument driver 1702. Rather, the second activating mechanism 1812b may include a motor 1816 operable to actuate the second activating mechanism 1812b. More specifically, the motor 1816 may be coupled or mounted to the carriage 1626 and thus able to travel with the carriage 1626 as the carriage 1626 moves along the longitudinal axis $A_1$. The motor 1816 may include or be operatively coupled to a drive gear 1818, such as through a drive shaft 1820, and the drive gear 1818 may be arranged to drive a driven gear 1822 that forms part of the second activating mechanism 1812b. Accordingly, operating the motor 1816 may cause the drive gear 1818 to rotate the driven gear 1822, and rotating the driven gear 1822 will actuate the second activating mechanism 1812b, as described below.

In some embodiments, the motor 1816 can include a plurality of motors 1816 operatively coupled with a gearbox, such as a planetary gearbox or a harmonic wave gear drive. The motor 1816 may comprise any type of prime mover or actuator that can be mounted to the carriage 1626 and is capable of rotating the drive shaft 1820 and thereby driving the drive gear 1818 in rotation. Suitable examples for the motor 1816 include, but are not limited to, a servo motor, a stepper motor, a DC brushless motor, or any combination thereof. The motor 1816 may also comprise any type of electromechanical actuator, such as a linear motor or a simple solenoid.

In some embodiments, the motor 1816 may be powered by an internal power source 1824*a* mounted to the carriage 1626 and configured to travel with the carriage 1626 while simultaneously powering the motor 1816. In such embodiments, the internal power source 1824*a* may comprise one or more batteries (rechargeable or non-rechargeable), fuel cells, capacitors, or any combination thereof. Suitable wiring and electrical connections may extend between the motor 1816 and the internal power source 1824*a* to facilitate the required transfer of electrical power to operate the motor 1816.

In other embodiments, however, the motor 1816 may alternatively be powered by an external power source 1824*b* located outside of the drive housing 1614. In such embodiments, an electrical line 1826 may extend from the drive housing 1614 (or another part of the surgical tool 1600 of FIG. 16) to connect the motor 1816 to the external power source 1824*b*. In some cases, the external power source 1824*b* may comprise electrical grid power derived from an adjacent wall outlet and the electrical line 1826 may terminate with an electrical plug connectable to the wall outlet. In other embodiments, however, the external power source 1824*b* may comprise an external battery, an electrosurgical generator, a fluidic power generator, a hydraulic power generator, a pneumatic power generator, or any combination thereof.

In some embodiments, the motor 1816 may be operable based on signals received at a receiver 1826 mounted or otherwise coupled to the carriage 1626. The receiver 1826 may be in wired or wireless communication with the robotic surgical system, which may transmit signals to the receiver 1826 when it is desired to operate the motor 1826 and thereby actuate (operate) the second activating mechanism 1812*b*. Suitable types of wireless communication include, but are not limited to, near field communication (NFC), radio frequency (RF), BLUETOOTH®, WiFi, infrared (IR), or any combination thereof.

In at least one embodiment, the second activating mechanism 1812*b* may further include an internal processor 1828, such as a computer system or microprocessor, in wired or wireless communication with the motor 1816, the internal power source 1824*a* (or external power source 1824*b*), and the receiver 1826. In such embodiments, the internal processor 1828 may be configured to regulate operation of the motor 1816 based on signals received from the receiver 1826. In some embodiments, the internal processor 1828 may alternatively (or in addition thereto) comprise a printed circuit board (PCB) that communicably couples the motor 1816, the internal power source 1824*a*, and the receiver 1826.

Incorporating the on-board motor 1816 may allow the second activating mechanism 1812*b* to carry out or perform high load or high torque functions of the surgical tool 1600 (FIG. 16) that may not be as efficient through operation of splines (e.g., the spline 1808). For example, functions such as articulating the end effector 1604 (FIG. 16) at the wrist 1606 (FIG. 16) typically require low input forces and result in low torque loading. Such low loading functions can be efficiently handled using splines, such as the spline 1808 driven by the second drive output 1806*b*. However, functions such as advancing or retracting a knife at the end effector 1604 or opening or closing the jaws 1610, 1612 (FIGS. 16 and 17A-17B) typically require higher loads that result in higher torques. For such high-load functions, it may prove advantageous to have the on-board motor 1816, which can provide elevated torque forces necessary to efficiently perform these functions. In at least one embodiment, the motor 1816 may include or otherwise be paired with a high ratio gearbox to further increase the torque output, without departing from the scope of the disclosure.

In at least one embodiment, the second activating mechanism 1812*b* may be configured to cause a knife (cutting element) at the end effector 1604 (FIGS. 16, 17B) to "fire", which, as discussed above, refers to advancing or retracting the knife at the end effector 1604. This can be accomplished by advancing or retracting a firing rod 1830, which may extend longitudinally through at least a portion of the carriage 1626 and may also extend along the longitudinal axis $A_1$ toward the end effector 1604. The knife is operatively coupled to the distal end of the firing rod 1830 such that longitudinal movement of the firing rod 1830 correspondingly moves the knife in the same direction. In some embodiments, the knife is directly coupled to the distal end of the firing rod 1830, but may alternatively be directly coupled to a firing member (not shown) that interposes the knife and the firing rod 1830. In either scenario, actuation of the second activating mechanism 1812*b* causes the knife to "fire", i.e., advance or retract.

In the illustrated embodiment, at least a portion of the firing rod 1830 may provide or otherwise define external threads 1832, and the driven gear 1822 may be rotatably mounted to the firing rod 1830 and configured to threadably engage the external threads 1832 with internal threads (not visible) defined on an inner surface of the driven gear 1822. In example operation of the second activating mechanism 1812*b*, the motor 1816 is activated to rotate the drive gear 1818, and the drive gear 1818 correspondingly rotates the driven gear 1822. Rotating the driven gear 1822 correspondingly drives the internal threads of the driven gear 1822 against the external threads 1832 of the firing rod 1830, and thereby advances or retracts the firing rod 1830 along the longitudinal axis $A_1$, depending on the rotational direction of the driven gear 1822. Longitudinal movement of the firing rod 1830 correspondingly moves the knife in the same direction at the end effector 1604 (FIGS. 16 and 17B).

Figure 19:
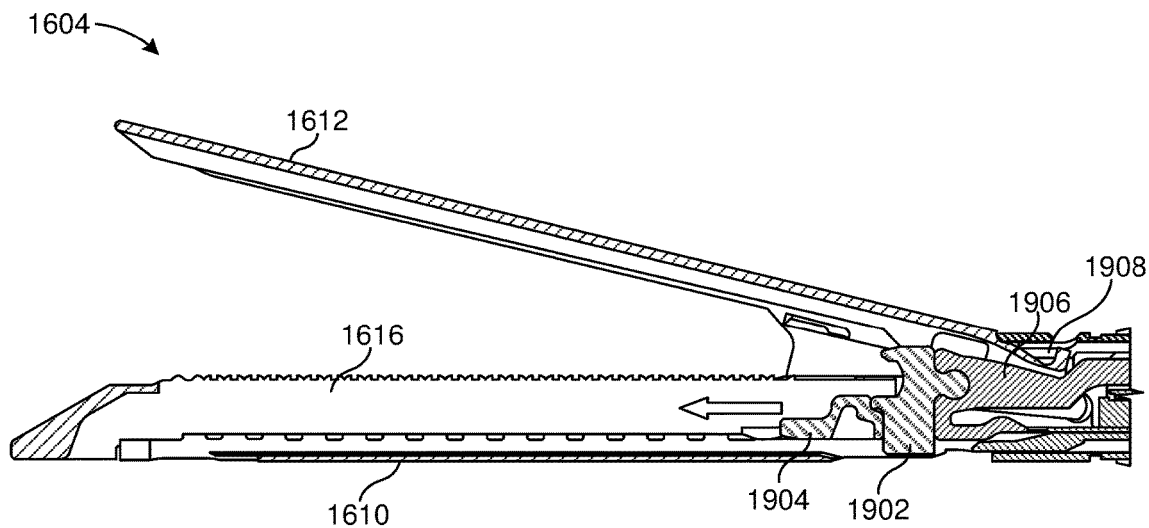
FIG. 19 is an enlarged cross-sectional view of the end effector of FIG. 16, according to one or more embodiments.

Referring to FIG. 19, with continued reference to FIG. 18, depicted is an enlarged cross-sectional view of the end effector 1604, according to one or more embodiments. As mentioned above, the end effector 1604 includes opposing jaws 1610, 1612 movable between open and closed positions, and the jaws 1610, 1612 are depicted in FIG. 19 in the open position. The end effector 1604 may further include a knife 1902 that can be linearly displaced within the slot 1616 defined in the second jaw 1610 to cut tissue grasped between the jaws 1610, 1612. As the knife 1902 advances distally within the slot 1616, a sled or camming wedge 1904 simultaneously engages a plurality of staples (not shown) contained within the first jaw 1610 (e.g., within a staple cartridge) and urges (cams) the staples into deforming contact with the opposing anvil surfaces (e.g., pockets) provided on the second jaw 1612. Properly deployed staples help seal opposing sides of the transected tissue.

As illustrated, the knife 1902 is operatively coupled to a firing member 1906 that extends proximally (i.e., to the right in FIG. 19) and is operatively coupled to the firing rod 1830 of FIG. 18 at its proximal end. In other embodiments, however, the knife 1902 may be directly coupled to the firing rod 1830, without departing from the scope of the disclosure. Actuation of the firing rod 1830, as generally described above, causes the firing member 1906 to advance and retract and correspondingly advance and retract the knife 1902 so that it can transect tissue grasped between the jaws 1610, 1612. Distal movement of the firing member 1906 also correspondingly moves the camming wedge 1904 to deploy the staples, as described above.

In some embodiments, movement of the firing rod 1830 (FIG. 18) in the distal direction may also cause the jaws 1610, 1612 to simultaneously close. More specifically, in one or more embodiments, the rod 1830 (or the firing member 1906) or the knife 1902 may include a feature or structure (not shown) configured to engage an anvil 1908 provided on the upper jaw 1612. In such embodiments, as the firing rod 1830 is advanced distally, the feature or structure will axially engage the angled surface of the anvil 1908 and force the second jaw 1612 to close.

Referring again to FIG. 18, in other embodiments, the second activating mechanism 1812b may be configured to open or close the jaws 1610, 1612 (FIGS. 16 and 17A-17B) at the end effector 1604 (FIGS. 16 and 17B). To accomplish this, rotation of the driven gear 1822, as driven by the drive gear 1818, may cause an outer portion of the shaft 1602, referred to herein as the "closure tube" 1834, to translate axially along the longitudinal axis $A_1$. In the illustrated embodiment, the driven gear 1822 may be operatively coupled to the closure tube 1834 via the firing rod 1830, which may be directly coupled to a proximal end of the closure tube 1834 or may otherwise form an integral part or extension thereof. In other embodiments, the driven gear 1822 may be arranged to directly engage external threads defined on the closure tube 1834. In either scenario, rotating the driven gear 1822 will correspondingly move the closure tube 1834 axially along the longitudinal axis $A_1$, and advancing the closure tube 1834 distally forces the jaws 1610, 1612 to close, and retracting the closure tube 1834 proximally allows the jaws 1610, 1612 to open. In at least one embodiment, the jaws 1610, 1612 may be spring-biased to the open position, and in such embodiments, retracting the closure tube 1834 will allow the jaws 1610, 1612 to move back to the open position under spring force. In at least one embodiment, however, actuating the second activating mechanism 1812b may also cause the knife 1902 (FIG. 19) to fire. In such embodiments, as the driven gear 1822 rotates, both the firing rod 1830 and the closure tube 1834 may be moved simultaneously along the longitudinal axis $A_1$, and thereby fire and close at the same time.

Figure 20:
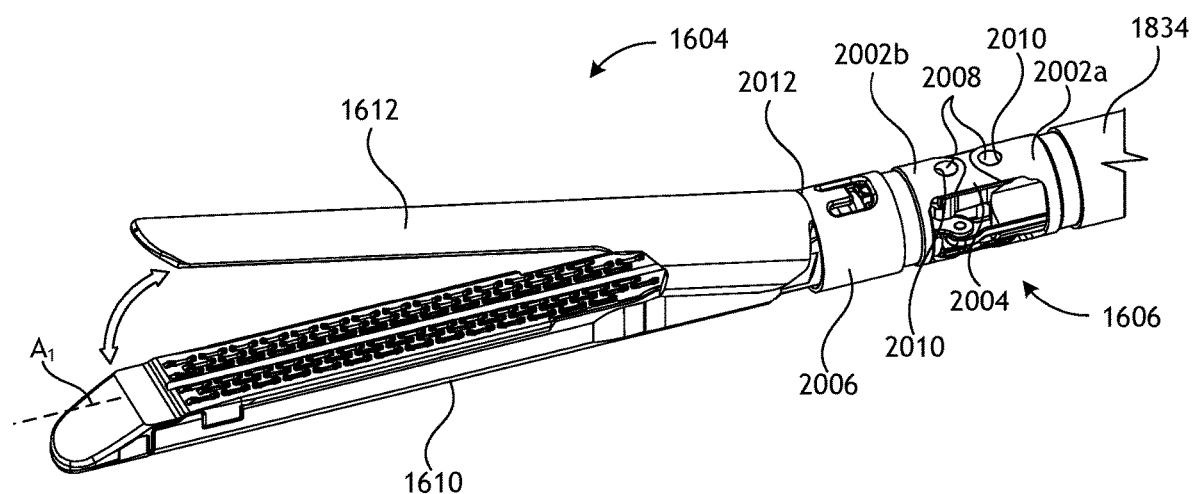
FIG. 20 is an enlarged view of the end effector and the wrist of FIG. 16, according to one or more embodiments.

Referring to FIG. 20, with continued reference to FIG. 18, depicted is an enlarged view of the end effector 1604 and the wrist 1606, according to one or more embodiments. As illustrated, the wrist 1606 may include a first or "proximal" clevis 2002a, a second or "distal" clevis 2002b, and a closure link 2004 configured to operatively couple the proximal and distal devises 2002a,b across the wrist 1606. The proximal clevis 2002a may be coupled to or otherwise form part of the distal end of the closure tube 1834, and the distal clevis 2002b may be coupled to or otherwise form part of a closure ring 2006.

Axial movement of the closure tube 1834 along the longitudinal axis $A_1$, as generally described above, correspondingly moves the proximal clevis 2002a in the same axial direction, and the closure link 2004 is configured to transmit the axial load through (across) the wrist 1606 to close the jaws 1610, 1612 of the end effector 1604. More specifically, the closure link 2004 defines a pair of protrusions 2008 configured to mate with corresponding apertures 2010 defined in each of the proximal and distal devises 2002a,b. The closure link 2004 may transmit the closure load or translation of the closure tube 1834 from the distal clevis 2002b to the proximal clevis 2002a and the closure ring 2006 will correspondingly push or pull on the upper jaw 1612 to open or close the upper jaw 1612. To close the upper jaw 1612, the closure ring 2006 is forced against a shoulder 2012 at or near the back of the upper jaw 1612, which urges the upper jaw 1612 to pivot down and to the closed position. To open the upper jaw 1612, the closure ring 2006 is retracted proximally by retracting the closure tube 1834, and the closure ring 2006 helps pull the upper jaw 1612 back toward the open position. Alternatively, the upper jaw 1612 may be spring loaded and biased to the open position, and retracting the closure ring 2006 removes loading on the shoulder 2012, which allows the spring force to move the upper jaw 1612 to the open position.

Hybrid Clamping and Firing with Embedded Motor on Translating Carriage

Figure 21:
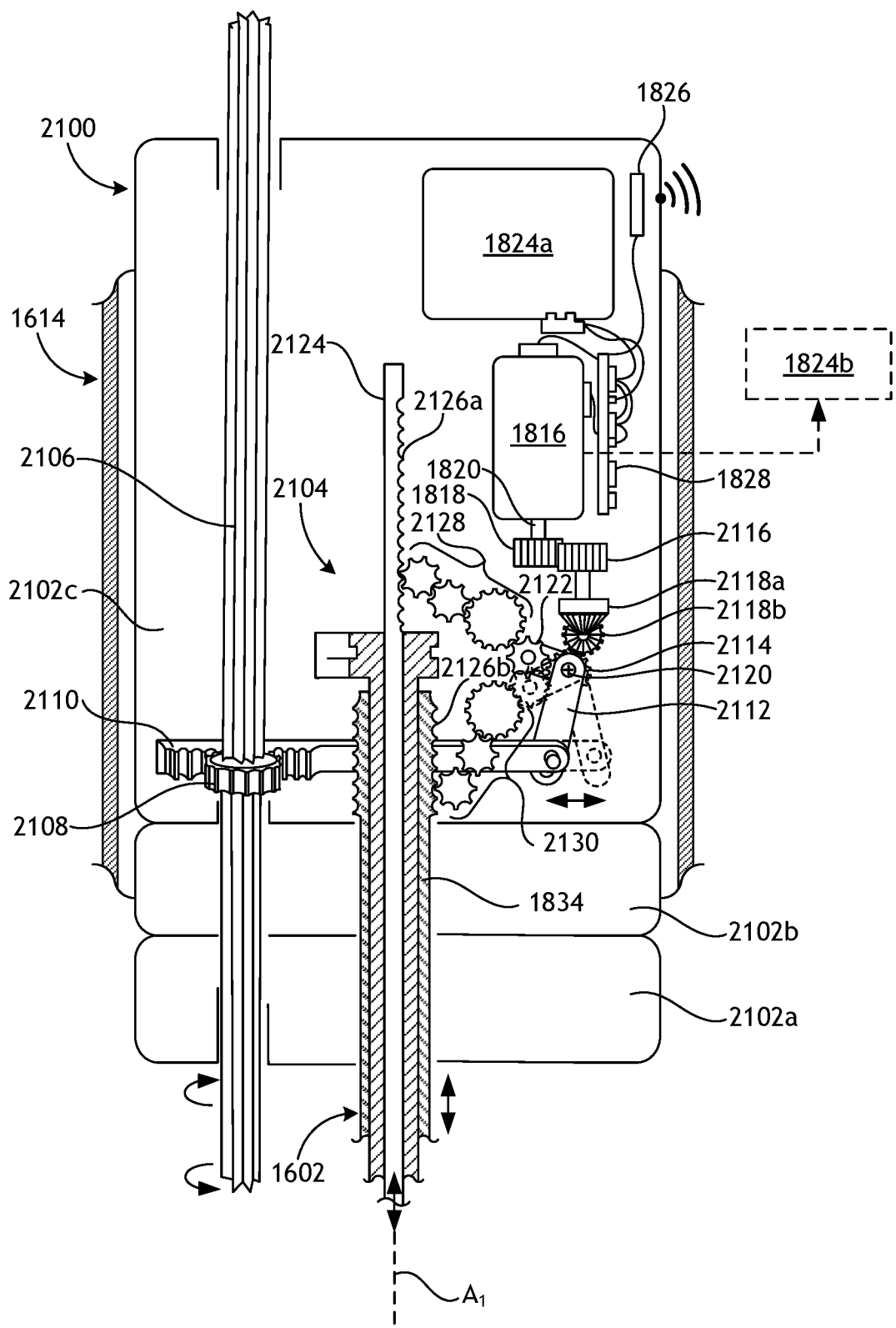
FIG. 21 is an enlarged view of an example carriage, according to one or more embodiments.

FIG. 21 is an enlarged view of an example carriage 2100, according to one or more embodiments. The carriage 2102 may be similar in some respects to the carriage 1626 of FIG. 16 and, therefore, may be used in conjunction with the drive housing 1614 generally described herein and may otherwise replace the carriage 1626. In the illustrated embodiment, the carriage 2100 includes three structural layers, shown as a first layer 2102a, a second layer 2102b, and a third layer 2102c. The layers 2102a-c may be similar in some respects to the layers 1628a-e of FIG. 16, and thus may house or contain an activating mechanism or otherwise help facilitate one or more functions of the surgical tool 1600 (FIG. 16). While the carriage 2100 includes three layers 2102a-c, the carriage 2100 may alternatively include more or less than three layers 2102a-c, without departing from the scope of the disclosure.

In the illustrated embodiment, an activating mechanism 2104 is housed in or otherwise secured to the carriage 2100 and, more particularly, to the third layer 2102c of the carriage 2100. The activating mechanism 2104 may be similar in some respects to the activating mechanisms 1638a-c described herein with reference to FIG. 16. Accordingly, the activating mechanism 2104 may be operable (actuatable) to carry out one or more functions of the end effector 1604 (FIGS. 16 and 17A-17B), such as opening or closing the jaws 1610, 1612 (FIGS. 16 and 17A-17B), articulating the end effector 1604 at the wrist 1606 (FIG. 16), or advancing or retracting a knife (e.g., the knife 1902 of FIG. 19) at the end effector 1604. The activating mechanism 2104 may be transitioned between a first state, where actuation of the activating mechanism 2104 performs a first function of the end effector 1604, and a second state, where actuation of the activating mechanism 2104 performs a second function of the end effector 1604 different from the first function. In the illustrated embodiment, actuating the activating mechanism 2104 when in the first state causes the knife to advance or retract, and actuating the activating mechanism 2104 when in the second state causes the jaws 1610, 1612 to open or close. While the present embodiment allows the activating mechanism 2104 to drive two functions of the end effector 1604, embodiments are contemplated herein where the activating mechanism 2104 is transitionable to perform more than two functions of the end effector 1604, without departing from the scope of the disclosure.

The activating mechanism 2104 includes a spline 2106 similar in some respects to the splines 1624a-c of FIG. 16. The carriage 2100 may be movably mounted to the spline 2106 (and a lead screw, not shown), and the spline 2106 may extend between and be rotatably mounted to the first and second ends 1618a,b (FIG. 16) of the drive housing 1614 (FIG. 16). Moreover, the spline 2106 may be operatively coupled to a drive input (not shown), similar to the drive inputs 1636a-d of FIGS. 16 and 17B, such that rotation of the drive input (via rotation of a corresponding drive output similar to the drive outputs 1724a-d of FIG. 17B) correspondingly rotates the spline 2106 in the same angular direction.

A pinion gear 2108 may be movably coupled to the spline 2106 and configured to rotate as the spline 2106 rotates. In some embodiments, the pinion gear 2108 may comprise a separate component part disposed about the spline 2106 and capable of translating (sliding) along the spline 2106 as the carriage 2100 moves along the longitudinal axis $A_1$. In other embodiments, however, the spline 2106 may be shaped and otherwise configured to operate as the pinion gear 2108 to advantageously reduce the number of component parts.

The spline 2106 is operatively coupled to the activating mechanism 2104 such that rotating the spline 2106 will correspondingly transition the activating mechanism 2104 between the first and second states. More particularly, the activating mechanism 2104 may further include a rack gear 2110 positioned to intermesh with the pinion gear 2108, and one end of the rack gear 2110 may be pivotally coupled to a transmission link 2112 pivotable (movable) between a first position, as shown in FIG. 21, and a second position as shown in the dashed (phantom) lines. When the transmission link 2112 is in the first position, the activating mechanism 2104 will effectively be in the first state and operable to perform the first function (e.g., advance or retract a knife). In contrast, when the transmission link 2112 is in the second position, the activating mechanism 2104 will effectively be in the second state and operable to perform the second function (e.g., open or close the jaws 1610, 1612 of FIGS. 16 and 17A-17B).

Unlike the activating mechanisms 1638a-c of FIG. 16, the activating mechanism 2104 is not operated or driven by a spline rotatable by a drive input (e.g., the drive inputs 1636a-d of FIGS. 16 and 17B) or through operation (actuation) of a drive output (e.g., the drive outputs 1724a-d of FIG. 17B). Rather, the activating mechanism 2104 is similar in some respects to the second activating mechanism 1812b of FIG. 18. More specifically, the activating mechanism 2104 includes the motor 1816 mounted to the carriage 2100 and thus able to travel with the carriage 2100 as the carriage 2100 translates along the longitudinal axis $A_1$. The motor 1816 drives the drive gear 1818 (i.e., via the drive shaft 1820), which causes actuation (operation) of the activating mechanism 2104 to perform either the first or second function.

In some embodiments, the motor 1816 may be powered by the internal power source 1824a mounted to the carriage 2100 and configured to travel with the carriage 2100 while simultaneously providing electrical power to the motor 1816. In other embodiments, however, the motor 1816 may alternatively be powered by the external power source 1824b located outside of the drive housing 1614, as generally described above. Moreover, the motor 1816 may be operable based on signals received at the receiver 1826 mounted or otherwise coupled to the carriage 2100, and the activating mechanism 2104 may further include the internal processor 1828 in wired or wireless communication with the motor 1816, the internal power source 1824a (or the external power source 1824b), and the receiver 1826.

Similar to the embodiment of FIG. 18 incorporating the on-board motor 1816 may allow the activating mechanism 2104 to carry out or perform high load or high torque functions of the surgical tool 1600 (FIG. 16) that may not be as efficient through operation of splines. For example, functions such as advancing or retracting a knife (e.g., the knife 1902 of FIG. 19) at the end effector 1604 or opening or closing the jaws 1610, 1612 (FIGS. 16 and 17A-17B) typically require higher loads that result in higher torques. For such high-load functions, the on-board motor 1816 will advantageously provide elevated torque forces necessary to efficiently perform these functions. Moreover, incorporating the motor 1816 will provide tool function when all the other tool drives are occupied for other tool functions.

In the illustrated embodiment, the drive gear 1818 is operatively coupled to a transmission drive gear 2114 rotatably mounted to the transmission link 2112 such that rotation of the drive gear 1818 correspondingly rotates the transmission drive gear 2114. In at least one embodiment, as illustrated, one or more intermediate gears or gear trains may interpose the drive gear 1818 and the transmission drive gear 2114. More specifically, as illustrated, the drive gear 1818 may be positioned to intermesh with a driven gear 2116, which may provide or otherwise define a first bevel gear 2118a at an opposing end. The first bevel gear 2118a may be positioned to intermesh with a second bevel gear 2118b positioned to intermesh with and drive the transmission drive gear 2114. In other embodiments, however, the driven gear 2116 may be omitted, and the first bevel gear 2118a may instead be provided on an opposing end of the drive gear 1818 to directly drive the second bevel gear 2118a, and thereby drive the transmission drive gear 2114. In yet other embodiments, the axes of rotation of the drive gear 1818 and the transmission drive gear 2114 may be parallel, thus eliminating the need for the bevel gears 2118a,b and a change in rotational axis. In such embodiments, the drive gear 1818 may directly drive the transmission drive gear 2114, without departing from the scope of the disclosure.

In the illustrated embodiment, the transmission link 2112 pivots about an axis of rotation 2120 extending through the transmission drive gear 2114, as acted upon by the rack gear 2110. Moreover, a transmission driven gear 2122 may also be mounted to the transmission link 2112 and driven by rotation of the transmission drive gear 2114. As the transmission link 2112 pivots between the first and second positions about the axis 2120, the transmission driven gear 2122 correspondingly pivots between a first position, as shown in FIG. 21, and a second position, as shown in the dashed (phantom) lines. When in the first position, the transmission driven gear 2122 may be positioned to operate the activating mechanism 2104 in the first state and thereby perform the first function of the end effector 1604 (FIGS. 16 and 17B). In contrast, when in the second position, the transmission driven gear 2122 may be positioned to operate the activating mechanism 2104 in the second state and thereby perform the second function of the end effector 1604.

When in the first state, the activating mechanism 2104 may be configured to cause a knife (e.g., the knife 1902 of FIG. 19) at the end effector 1604 (FIGS. 16, 17B) to "fire", which, as discussed above, refers to advancing or retracting the knife at the end effector 1604. This can be accomplished by advancing or retracting a firing rod 2124, which may extend longitudinally through at least a portion of the carriage 2100 and may also extend along the longitudinal axis $A_1$ toward the end effector 1604. The knife is operatively coupled to the distal end of the firing rod 2124 such that longitudinal movement of the firing rod 2124 correspondingly moves the knife in the same direction. In some embodiments, the knife is directly coupled to the distal end of the firing rod 2124, but may alternatively be directly coupled to a firing member (not shown) that interposes the knife and the firing rod 2124. In either scenario, actuation of the activating mechanism 2104 causes the knife to "fire", i.e., advance or retract.

In the illustrated embodiment, at least a portion of the firing rod 2124 may provide or otherwise define first external threads 2126a, and the transmission driven gear 2122 may be operable to drive the firing rod 2124 axially along the longitudinal axis $A_1$ at the first external threads 2126a. In some embodiments, as illustrated, the first external threads 2126a may comprise a rack gear drivable through rotation of the transmission driven gear 2122. In some embodiments, for example, the gear teeth of the transmission driven gear 2122 may directly engage and intermesh with the gear teeth of the first external threads 2126a such that rotation of the transmission driven gear 2122 correspondingly drives against the first external threads 2126a and thereby advances or retracts the firing rod 2124, depending on the rotational direction of the transmission driven gear 2122. In other embodiments, as illustrated, a gear train 2128 may interpose and otherwise extend between the transmission driven gear 2122 and the first external threads 2126a, and the driven gear 2122 may be operable to drive the gear train 2128, which correspondingly engages the first external threads 2126a and thereby advances or retracts the firing rod 2124. In the illustrated embodiment, the gear train 2128 includes three gears arranged in series, but could alternatively comprise more or less than three gears.

When in the second state, the activating mechanism 2104 may be configured to open or close the jaws 1610, 1612 (FIGS. 16 and 17A-17B) at the end effector 1604 (FIGS. 16 and 17B). This can be accomplished by advancing or retracting the closure tube 1834 of the shaft 1602. In the illustrated embodiment, at least a portion of the closure tube 1834 may provide or otherwise define second external threads 2126b, and the transmission driven gear 2122 may be operable to drive the closure tube 1834 axially along the longitudinal axis $A_1$ at the second external threads 2126b. In some embodiments, as illustrated, the second external threads 2126b may comprise a rack gear drivable through rotation of the transmission driven gear 2122. In some embodiments, for example, the gear teeth of the transmission driven gear 2122 may directly engage and intermesh with the gear teeth of the second external threads 2126b such that rotation of the transmission driven gear 2122 correspondingly drives against the second external threads 2126b, and thereby advances or retracts the closure tube 1834, depending on the rotational direction of the transmission driven gear 2122. In other embodiments, as illustrated, a gear train 2130 may interpose and otherwise extend between the transmission driven gear 2122 and the second external threads 2126b and the driven gear 2122 may be operable to drive the gear train 2130, which correspondingly engages the second external threads 2126b and thereby advances or retracts the closure tube 1834. In the illustrated embodiment, the gear train 2128 includes three gears arranged in series, but could alternatively comprise more or less than three gears. In either scenario, rotating the transmission driven gear 2122 will correspondingly move the closure tube 1834 axially along the longitudinal axis $A_1$, and advancing the closure tube 1834 distally forces the jaws 1610, 1612 to close, and retracting the closure tube 1834 proximally allows the jaws 1610, 1612 to open.

Figure 22:
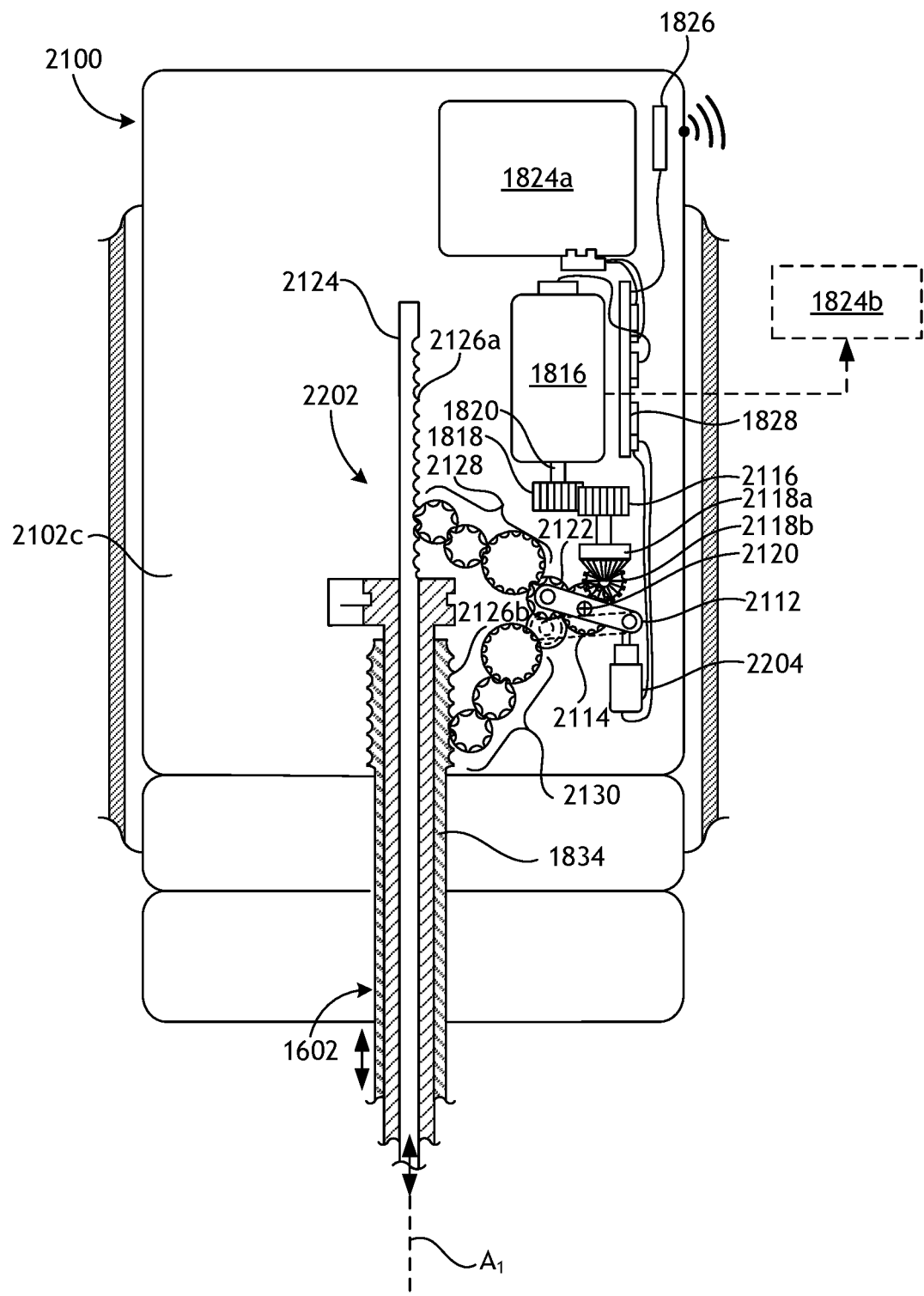
FIG. 22 is an enlarged view of another embodiment of the carriage of FIG. 21, according to one or more additional embodiments.

FIG. 22 is an enlarged view of another embodiment of the carriage 2100 of FIG. 21, according to one or more additional embodiments. In the illustrated embodiment, an activating mechanism 2202 is housed in or otherwise secured to the carriage 2100 and, more particularly, to the third layer 2102c of the carriage 2100. The activating mechanism 2202 may be similar in some respects to the activating mechanism 2104 of FIG. 21 and, therefore, may be best understood with reference thereto, where like numerals will correspond to like components not described again.

Similar to the activating mechanism 2104 of FIG. 21, for example, the activating mechanism 2202 may be transitioned between a first state, where actuation of the activating mechanism 2202 performs a first function (e.g., causes a knife to advance or retract), and a second state, where actuation of the activating mechanism 2202 performs a second function (e.g., causes the jaws to open or close). Moreover, the activating mechanism 2202 includes the motor 1816 mounted to the carriage 2100 and thus able to travel with the carriage 2100 as the carriage 2100 translates along the longitudinal axis $A_1$. The motor 1816 drives the drive gear 1818 (i.e., via the drive shaft 1820), which causes actuation (operation) of the activating mechanism 2202 to perform either function. Moreover, the motor 1816 can be powered by the internal power source 1824a or the external power source 1824b, as generally described above, and the motor 1816 may be operable based on signals received at the receiver 1826. The activating mechanism 2202 may further include the internal processor 1828 in wired or wireless communication with the motor 1816, the internal power source 1824a (or the external power source 1824b), and the receiver 1826.

Unlike the activating mechanism 2104 of FIG. 21, however, the activating mechanism 2202 does not incorporate the use of a spline to transition the activating mechanism 2202 between the first and second states. Instead, the activating mechanism 2104 includes an actuator 2204 operatively coupled to the transmission link 2112 and operable to pivot the transmission link 2112 about the axis of rotation 2120 and between the first position, as shown in FIG. 22, and the second position as shown in the dashed (phantom) lines.

The actuator 2204 may comprise any device operable to pivot the transmission link 2112 between the first and second positions. In at least one embodiment, the actuator 2204 may comprise a solenoid shifter or a multi-position servo. The actuator 2204 may be communicably coupled to the internal processor 1828, which may control operation of the actuator 2204 based on signals received from the receiver 1826. Moreover, the actuator 2204 may be powered by the internal or external power sources 1824a,b.

When the transmission link 2112 is in the first position, the activating mechanism 2202 will effectively be in the first state and operable to perform the first function. In contrast, when the transmission link 2112 is in the second position, as shown in dashed lines, the activating mechanism 2202 will effectively be in the second state and operable to perform the second function. As discussed above, the drive gear 1818 is operatively coupled to the transmission drive gear 2114 such that rotation of the drive gear 1818 correspondingly rotates the transmission drive gear 2114. In some embodiments, as discussed above, one or more gears may interpose the drive gear 1818 and the transmission drive gear 2114, such as the driven gear 2116 and the first and second bevel gears 2118a,b. In other embodiments, however, the drive gear 1818 may be arranged ad configured to directly drive the transmission drive gear 2114, without departing from the scope of the disclosure.

As the transmission link 2112 pivots about the axis of rotation 2120 extending through the transmission drive gear 2114, as acted upon by the actuator 2204, the transmission driven gear 2122 will correspondingly pivot between the first and second positions. When in the first position, the transmission driven gear 2122 may be positioned to operate the activating mechanism 2202 in the first state and thereby advance or retract a knife (e.g., the knife 1902 of FIG. 19). More specifically, the knife can be fired by advancing or retracting the firing rod 2124, and the transmission driven gear 2122 may be operable to drive the firing rod 2124 axially along the longitudinal axis $A_1$ by engaging the first external threads 2126a. In some embodiments, as mentioned above, the transmission driven gear 2122 may be positioned to directly engage the first external threads 2126a such that rotation of the transmission driven gear 2122 correspondingly drives against the first external threads 2126a. In other embodiments however, the gear train 2128 may interpose and otherwise extend between the transmission driven gear 2122 and the first external threads 2126a, and the driven gear 2122 may drive the gear train 2128, which correspondingly drives the first external threads 2126a.

In contrast, when in the second position, the transmission driven gear 2122 may be positioned to operate the activating mechanism 2202 in the second state and thereby open or close the jaws 1610, 1612 (FIGS. 16 and 17A-17B) at the end effector 1604 (FIGS. 16 and 17B). More specifically, the transmission driven gear 2122 may be operable to advance or retract the closure tube 1834 of the shaft 1602 by driving against the second external threads 2126b defined on the closure tube 1834. In some embodiments, as mentioned above, the transmission driven gear 2122 may be positioned to directly engage and drive the second external threads 2126b such that rotation of the transmission driven gear 2122 correspondingly drives against the second external threads 2126b. In other embodiments, however, the gear train 2130 may interpose and otherwise extend between the transmission driven gear 2122 and the second external threads 2126b, which correspondingly drives the second external threads 2126b to advance or retract the closure tube 1834.

Figure 23:
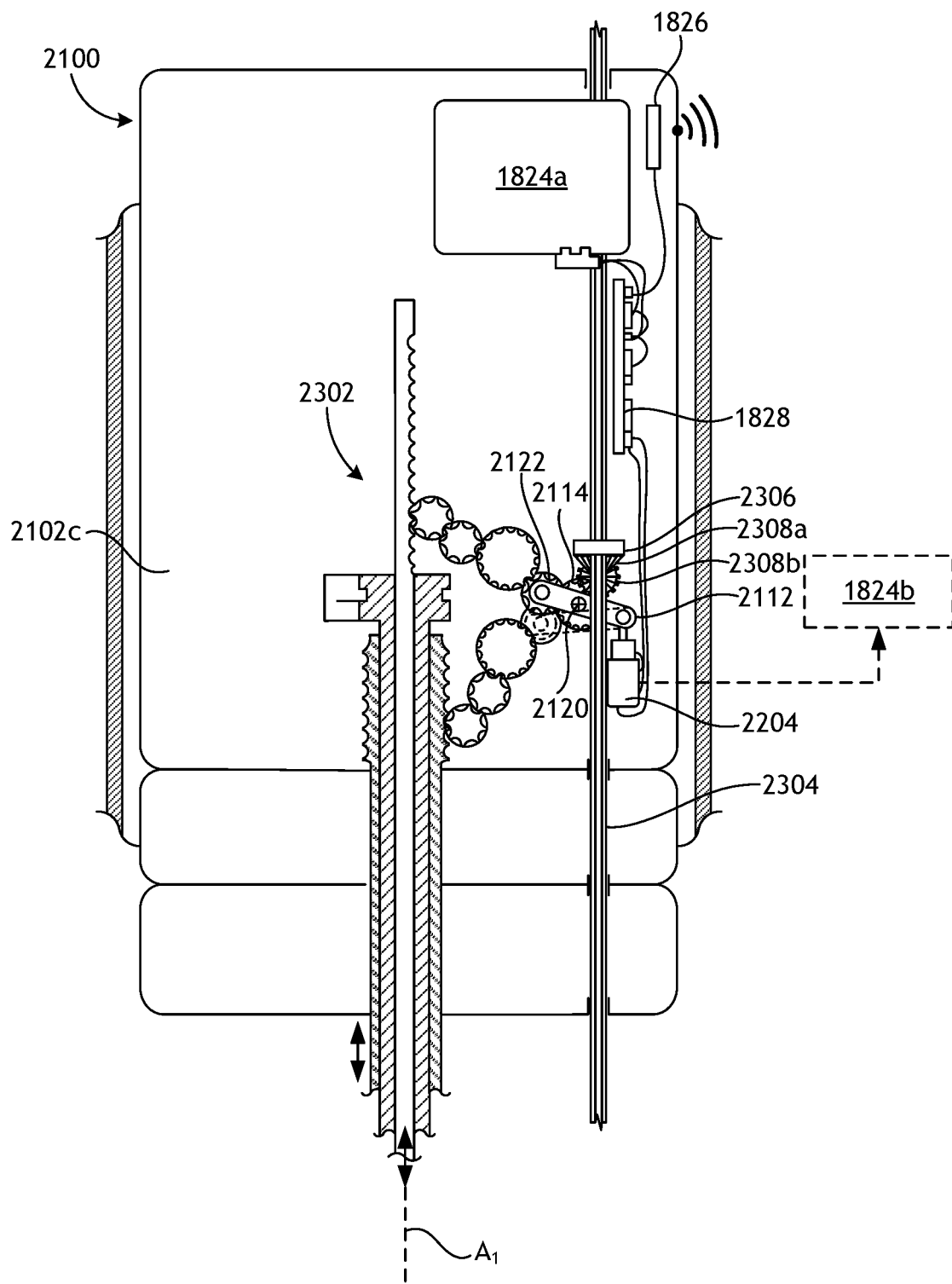
FIG. 23 is an enlarged view of another embodiment of the carriage of FIG. 21, according to one or more additional embodiments.

FIG. 23 is an enlarged view of another embodiment of the carriage 2100 of FIG. 21, according to one or more additional embodiments. In the illustrated embodiment, an activating mechanism 2302 is housed in or otherwise secured to the carriage 2100 and, more particularly, to the third layer 2102c of the carriage 2100. The activating mechanism 2302 may be similar in some respects to the activating mechanisms 2104, 2202 of FIGS. 21 and 22, respectively, and therefore may be best understood with reference thereto, where like numerals will correspond to like components not described again.

Similar to the activating mechanisms 2104, 2202, for example, the activating mechanism 2302 may be transitioned between a first state, where actuation of the activating mechanism 2302 performs a first function (e.g., causes a knife to advance or retract), and a second state, where actuation of the activating mechanism 2302 performs a second function (e.g., causes jaws to open or close). Moreover, the activating mechanism 2104 includes the actuator 2204 used to pivot the transmission link 2112 between the first and second positions, and thereby transition the activating mechanism 2302 between the first and second states. The actuator 2204 may be communicably coupled to the internal processor 1828, which controls operation of the actuator 2204 based on signals received from the receiver 1826, and the actuator 2204 may be powered by the internal or external power sources 1824a, b.

Unlike the activating mechanism 2202 of FIG. 22, however, the activating mechanism 2302 does not include the motor 1816 (FIGS. 21-22) to drive the transmission drive gear 2114 mounted to the transmission link 2112. Instead, the activating mechanism 2302 includes a spline 2304 similar in some respects to the splines 1624a-c of FIG. 16. The carriage 2100 may be movably mounted to the spline 2304, and the spline 2304 may extend between and be rotatably mounted to the first and second ends 1618a,b (FIG. 16) of the drive housing 1614 (FIG. 16). Moreover, the spline 2304 may be operatively coupled to a drive input (not shown), similar to the drive inputs 1636a-d of FIGS. 16 and 17B, such that rotation of the drive input (via rotation of a corresponding drive output similar to the drive outputs 1724a-d of FIG. 17B) correspondingly rotates the spline 2304 in the same angular direction.

A drive gear 2306 may be movably coupled to the spline 2304 and configured to rotate as the spline 2304 rotates. In some embodiments, the drive gear 2306 may comprise a separate component part disposed about the spline 2304 and capable of translating (sliding) along the spline 2304 as the carriage 2100 moves along the longitudinal axis $A_1$. In other embodiments, however, the spline 2304 may be shaped and otherwise configured to operate as the drive gear 2306 to advantageously reduce the number of component parts.

The drive gear 2306 may be operatively coupled to the transmission drive gear 2114 such that rotation of the drive gear 2306 correspondingly rotates the transmission drive gear 2114. In some embodiments, the drive gear 2306 may engage and directly drive the transmission drive gear 2114. In other embodiments, however, one or more gears may interpose the drive gear 2306 and the transmission drive gear 2114. In the illustrated embodiment, for example, the drive gear 2306 may comprise a first bevel gear 2308a, similar to the first bevel gear 2118a of FIGS. 21 and 22, and may be positioned to intermesh with a second bevel gear 2308b, similar to the second bevel gear 2118b of FIGS. 21 and 22. The second bevel gear 2308b may be positioned to intermesh with the transmission drive gear 2114 such that rotation of the drive gear 2306 correspondingly rotates the transmission drive gear 2114.

As the transmission link 2112 pivots about the axis of rotation 2120 extending through the transmission drive gear 2114, as acted upon by the actuator 2204, the transmission driven gear 2122 will correspondingly pivot between the first and second positions. When in the first position, the transmission driven gear 2122 may be positioned to operate the activating mechanism 2302 in the first state and thereby advance or retract a knife (e.g., the knife 1902 of FIG. 19), as generally described above with reference to FIG. 22. In contrast, when in the second position, the transmission driven gear 2122 may be positioned to operate the activating mechanism 2302 in the second state and thereby open or close the jaws 1610, 1612 (FIGS. 16 and 17A-17B) at the end effector 1604 (FIGS. 16 and 17B), as also generally described above with reference to FIG. 22.

4. Implementing Systems and Terminology

The specific computer-implemented processes/functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
a drive housing having opposing first and second ends, and a carriage mounted within the drive housing and axially translatable between the first and second ends;
an elongate shaft extending from the carriage and penetrating the first end, the shaft having an end effector arranged at a distal end thereof; and
an activating mechanism secured to the carriage and including:
a transmission link pivotably coupled to the carriage at a pivot axis;
a transmission drive gear rotatably mounted to the transmission link at the pivot axis;
a drive gear rotatably mounted to the carriage and operatively coupled to the transmission drive gear such that rotation of the drive gear correspondingly rotates the transmission drive gear; and
a transmission driven gear rotatably mounted to the transmission link and driven by rotation of the transmission drive gear,
wherein the transmission link is pivotable about the pivot axis between a first position, where the transmission driven gear is arranged to actuate the activating mechanism to perform a first function of the end effector, and a second position, where the transmission driven gear is arranged to actuate the activating mechanism to perform a second function of the end effector different from the first function.

2. The robotic surgical tool of claim 1, further comprising a motor mounted to the carriage and operable to drive the drive gear.

3. The robotic surgical tool of claim 2, wherein the activating mechanism further includes:
a power source communicably coupled to the motor to provide electrical power to the motor;
a receiver that receives signals for operation of the motor; and
an internal processor communicably coupled to the motor, the power source, and the receiver to regulate operation of the motor based on the signals received from the receiver.

4. The robotic surgical tool of claim 3, wherein the power source is an internal power source mounted to the carriage for travel with the carriage.

5. The robotic surgical tool of claim 3, wherein the power source is an external power source disposed outside of the drive housing.

6. The robotic surgical tool of claim 1, wherein the activating mechanism further comprises:
a spline extending between the first and second ends;
a pinion gear movably coupled to the spline and rotatable with rotation of the spline; and
a rack gear pivotably coupled to the transmission link and positioned to engage the pinion gear,
wherein rotation of the spline correspondingly rotates the pinion gear to drives the rack gear and thereby pivot the transmission link between the first and second positions.

7. The robotic surgical tool of claim 6, further comprising:
a drive input arranged at the first end and operatively coupled to the spline such that rotation of the drive input correspondingly rotates the spline and the pinion drive gear; and
an instrument driver arranged at an end of a robotic arm and matable with the drive housing at the first end, the instrument driver providing a drive output matable with the drive input such that rotation of the drive output correspondingly rotates the drive input and thereby transitions the transmission link between the first and second positions.

8. The robotic surgical tool of claim 1, further comprising:
a firing rod extending within the shaft and defining external threads; and
a knife located at the end effector and operatively coupled to the firing rod such that movement of the firing rod correspondingly moves the knife in the same direction, wherein, when the transmission link is in the first position, rotation of the transmission driven gear drives the external threads of the firing rod and thereby moves the firing rod and the knife longitudinally.

9. The robotic surgical tool of claim 1, wherein the shaft comprises a closure tube that defines external threads, and wherein, when the transmission link is in the second position, rotation of the transmission driven gear drives the external threads and thereby moves the closure tube axially along a longitudinal axis of the shaft to close or open jaws of the end effector.

10. The robotic surgical tool of claim 1, wherein the activating mechanism further comprises an actuator operatively coupled to the transmission link and operable to pivot the transmission link between the first and second positions.

11. The robotic surgical tool of claim 1, further comprising:
a spline extending between the first and second ends, the drive gear being movably coupled to the spline and rotatable with rotation of the spline;
a drive input arranged at the first end and operatively coupled to the spline such that rotation of the drive input correspondingly rotates the spline and the drive gear; and
an instrument driver arranged at an end of a robotic arm and matable with the drive housing at the first end, the instrument driver providing a drive output matable with the drive input such that rotation of the drive output correspondingly rotates the drive input and thereby actuates the activating mechanism.

12. The robotic surgical tool of claim 1, wherein the end effector is selected from the group consisting of a surgical stapler, a tissue grasper, surgical scissors, an advanced energy vessel sealer, a clip applier, a needle driver, a babcock including a pair of opposed grasping jaws, bipolar jaws, a suction irrigator, an endoscope, a laparoscope, a probe, a scope, an advanced imaging system, and any combination thereof.

13. A method, comprising:
locating a robotic surgical tool adjacent a patient, the robotic surgical tool comprising:
a drive housing having opposing first and second ends, and a carriage mounted within the drive housing and axially translatable between the first and second ends;
an elongate shaft extending from the carriage and penetrating the first end, the shaft having an end effector arranged at a distal end thereof; and
an activating mechanism secured to the carriage and including a transmission link pivotably coupled to the carriage at a pivot axis, a transmission drive gear rotatably mounted to the transmission link at the pivot axis, a drive gear rotatably mounted to the carriage and operatively coupled to the transmission drive gear, and a transmission driven gear rotatably mounted to the transmission link;
pivoting the transmission link about the pivot axis between a first position, where the transmission driven gear is arranged to actuate the activating mechanism to perform a first function of the end effector, and a second position, where the transmission driven gear is arranged to actuate the activating mechanism to perform a second function of the end effector different from the first function; and
actuating the drive gear to rotate the transmission drive gear and thereby drive the driven gear to perform the first or second function.

14. The method of claim 13, wherein actuating the drive gear comprises:
operating a motor mounted to the carriage, the drive gear being operatively coupled to the motor;
providing electrical power to the motor with a power source communicably coupled to the motor;
receiving signals that control operation of the motor at a receiver; and
regulating operation of the motor based on the signals received from the receiver with an internal processor communicably coupled to the motor, the power source, and the receiver.

15. The method of claim 14, wherein the power source is an internal power source mounted to the carriage, the method further comprising carrying the power source with the carriage as the carriage moves longitudinally.

16. The method of claim 13, wherein the activating mechanism further comprises a spline extending between the first and second ends, a pinion gear movably coupled to the spline and rotatable with rotation of the spline, and a rack gear pivotably coupled to the transmission link and positioned to engage the pinion gear, and wherein pivoting the transmission link between the first and second positions comprises:
rotating the spline and thereby rotating the pinion gear to drive the rack gear to pivot the transmission link between the first and second positions.

17. The method of claim 13, wherein the robotic surgical tool further comprises a firing rod extending within the shaft and defining external threads, and a knife located at the end effector and operatively coupled to the firing rod, and wherein actuating the drive gear comprises:
rotating the transmission driven gear in the first position and thereby driving the firing rod at the external threads; and
moving the firing rod and the knife longitudinally as the transmission driven gear rotates.

18. The method of claim 13, wherein the shaft comprises a closure tube that defines external threads, and wherein actuating the drive gear comprises:
rotating the transmission driven gear in the first position and thereby driving the closure tube at the external threads; and
moving the closure gear axially along a longitudinal axis of the shaft and thereby closing or opening jaws of the end effector.

19. The method of claim 13, wherein pivoting the transmission link between the first and second positions comprises operating an actuator operatively coupled to the transmission link, the actuator being operatively coupled to the transmission link.

20. The method of claim 13, wherein the activating mechanism further a spline extending between the first and second ends, the drive gear being movably coupled to the spline and rotatable with rotation of the spline, and wherein actuating the drive gear comprises rotating the spline and thereby rotating the drive gear.

* * * * *